United States Patent

Guay et al.

(10) Patent No.: US 6,743,802 B2
(45) Date of Patent: Jun. 1, 2004

(54) ALKYNE-ARYL PHOSPHODIESTERASE-4 INHIBITORS

(75) Inventors: Daniel Guay, Ile-Perrot (CA); Mario Girard, Saint-Lazare (CA); Pierre Hamel, Vimont-Laval (CA); Sebastien Laliberte, Ile Perrot (CA); Richard Friesen, Kirkland (CA)

(73) Assignee: Merck Frosst Canada & Co., Kirkland (CA)

( * ) Notice: Subject to any disclaimer, the term of this patent is extended or adjusted under 35 U.S.C. 154(b) by 0 days.

(21) Appl. No.: 10/226,980

(22) Filed: Aug. 23, 2002

(65) Prior Publication Data

US 2003/0114478 A1 Jun. 19, 2003

Related U.S. Application Data

(60) Provisional application No. 60/316,093, filed on Aug. 29, 2001.

(51) Int. Cl.⁷ .................. A61K 31/4375; C07D 471/04
(52) U.S. Cl. ........................................ 514/300; 546/123
(58) Field of Search ........................... 546/123; 514/300

(56) References Cited

FOREIGN PATENT DOCUMENTS

| EP | 0 978 516 A1 | 2/2000 |
| WO | WO 99/07704 | 2/1899 |
| WO | 99/07704 | * 2/1999 |
| WO | WO 99/09504 | 2/2000 |

OTHER PUBLICATIONS

Matsuura, et al., Biological & Pharmaceutical Bulletin, vol. 17, No. 4, pp. 498–503, 1994.

* cited by examiner

*Primary Examiner*—Patricia L. Morris
(74) *Attorney, Agent, or Firm*—Curtis C. Panzer; David L. Rose

(57) ABSTRACT

Compounds represented by Formula (I):

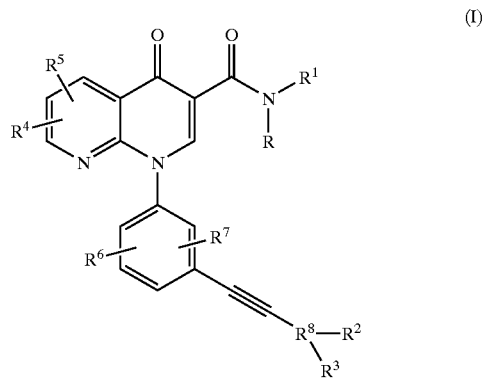

or a pharmaceutically acceptable salt thereof, are phosphodiesterase 4 inhibitors useful in the treatment of asthma and inflammation.

16 Claims, No Drawings

ALKYNE-ARYL PHOSPHODIESTERASE-4 INHIBITORS

BACKGROUND OF THE INVENTION

This application claims benefit of priority of provisional application, serial No. 60/316,093, filed Aug. 29, 2001.

FIELD OF THE INVENTION

The present invention is directed to compounds that are alkyne-aryl substituted 1,8-naphthyridin-4(1H)-ones. In particular, this invention is directed to phenyl substituted 1,8-naphthyridin-4(1H)-ones which are phosphodiesterase-4 inhibitors wherein the phenyl group is at the 1-position and contains a 2-alkyne substituent group further optionally substituted.

RELATED BACKGROUND

Hormones are compounds that variously affect cellular activity. In many respects, hormones act as messengers to trigger specific cellular responses and activities. Many effects produced by hormones, however, are not caused by the singular effect of just the hormone. Instead, the hormone first binds to a receptor, thereby triggering the release of a second compound that goes on to affect the cellular activity. In this scenario, the hormone is known as the first messenger while the second compound is called the second messenger. Cyclic adenosine monophosphate (adenosine 3',5'-cyclic monophosphate, "cAMP" or "cyclic AMP") is known as a second messenger for hormones including epinephrine, glucagon, calcitonin, corticotrophin, lipotropin, luteinizing hormone, norepinephrine, parathyroid hormone, thyroid-stimulating hormone, and vasopressin. Thus, cAMP mediates cellular responses to hormones. Cyclic AMP also mediates cellular responses to various neurotransmitters.

Phosphodiesterases ("PDE") are a family of enzymes that metabolize 3',5' cyclic nucleotides to 5' nucleoside monophosphates, thereby terminating cAMP second messenger activity. A particular phosphodiesterase, phosphodiesterase-4 ("PDE4", also known as "PDE-IV"), which is a high affinity, cAMP specific, type IV PDE, has generated interest as potential targets for the development of novel anti-asthmatic and anti-inflammatory compounds. PDE4 is known to exist as at lease four isoenzymes, each of which is encoded by a distinct gene. Each of the four known PDE4 gene products is believed to play varying roles in allergic and/or inflammatory responses. Thus, it is believed that inhibition of PDE4, particularly the specific PDE4 isoforms that produce detrimental responses, can beneficially affect allergy and inflammation symptoms. It would be desirable to provide novel compounds and compositions that inhibit PDE4 activity.

A major concern with the use of PDE4 inhibitors is the side effect of emesis which has been observed for several candidate compounds as described in C. Burnouf et al., ("Burnouf"), *Ann. Rep. In Med. Chem.*, 33:91–109(1998). B. Hughes et al., *Br. J.Pharmacol.*, 118:1183–1191(1996); M. J. Perry et al., *Cell Biochem. Biophys.*, 29:113–132(1998); S. B. Christensen et al., *J.Med. Chem.*, 41:821–835(1998); and Burnouf describe the wide variation of the severity of the undesirable side effects exhibited by various compounds. As described in M. D. Houslay et al., *Adv. In Pharmacol.*, 44:225–342(1998) and D. Spina et al., *Adv. In Pharmacol.*, 44:33–89(1998), there is great interest and research of therapeutic PDE4 inhibitors.

International Patent Publication WO9422852 describes quinolines as PDE inhibitors. International Patent Publication WO9907704 describes 1-aryl-1,8-naphthylidin-4-one derivatives as PDE4 inhibitors.

A.H. Cook, et al., *J.Chem. Soc.*, 413–417(1943) describes gamma-pyridylquinolines. Other quinoline compounds are described in Kei Manabe et al., *J.Org. Chem.*, 58(24):6692–6700(1993); Kei Manabe et al., *J.Am. Chem. Soc.*, 115(12):5324–5325(1993); and Kei Manabe et al., *J.Am. Chem. Soc.*, 114(17):6940–6941(1992).

Compounds that include ringed systems are described by various investigators as effective for a variety of therapies and utilities. For example, International Patent Publication No. WO 98/25883 describes ketobenzamides as calpain inhibitors, European Patent Publication No. EP 811610 and U.S. Pat. Nos. 5,679,712, 5,693,672 and 5,747,541 describe substituted benzoylguanidine sodium channel blockers, U.S. Pat. No. 5,736,297 describes ring systems useful as a photosensitive composition.

U.S. Pat. Nos. 5,491,147, 5,608,070, 5,622,977, 5,739,144, 5,776,958, 5,780,477, 5,786,354, 5,798,373, 5,849,770, 5,859,034, 5,866,593, 5,891,896, and International Patent Publication WO 95/35283 describe PDE4 inhibitors that are tri-substituted aryl or heteroaryl phenyl derivatives. U.S. Pat. No. 5,580,888 describes PDE4 inhibitors that are styryl derivatives. U.S. Pat. No. 5,550,137 describes PDE4 inhibitors that are phenylaminocarbonyl derivatives. U.S. Pat. No. 5,340,827 describes PDE4 inhibitors that are phenylcarboxamide compounds. U.S. Pat. No. 5,780,478 describes PDE4 inhibitors that are tetra-substituted phenyl derivatives. International Patent Publication WO 96/00215 describes substituted oxime derivatives useful as PDE4 inhibitors. U.S. Pat. No. 5,633,257 describes PDE4 inhibitors that are cyclo(alkyl and alkenyl)phenyl-alkenyl (aryl and heteroaryl) compounds.

However, there remains a need for novel compounds and compositions that therapeutically inhibit PDE4 with minimal side effects.

SUMMARY OF THE INVENTION

The present invention is directed to alkyne-aryl substituted 1,8-naphthyridin-4(1H)-ones represented by Formula (I):

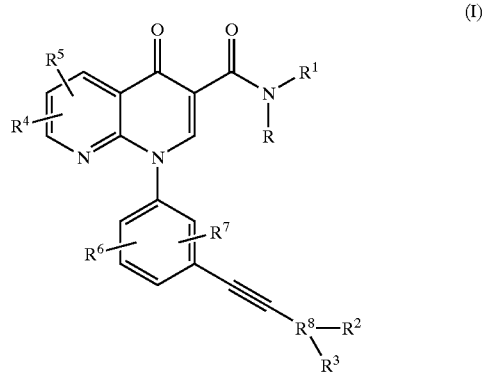

or pharmaceutically acceptable salts thereof, which are phosphodiesterase-4 inhibitors.

This invention also provides a pharmaceutical composition which includes an effective amount of the novel alkyne-aryl substituted 1,8-naphthyridin-4(1H)-ones and a pharmaceutically acceptable carrier. This invention further provides a method of treatment in mammals of, for example, i) Pulmonary disorders such as asthma, chronic bronchitis, chronic obstructive pulmonary disease (COPD), adult respiratory distress syndrome, infant respiratory distress syndrome, cough, chronic obstructive pulmonary disease in animals, adult respiratory distress syndrome, and infant respiratory distress syndrome, ii) Gastrointestinal disorders such as ulcerative colitis, Crohn's disease, and hypersecretion of gastric acid, iii) Infectious diseases such as bacterial, fungal or viral induced sepsis or septic shock, endotoxic shock (and associated conditions such as laminitis and colic in horses), and septic shock, iv) Neurological disorders such as spinal cord trauma, head injury, neurogenic inflammation, pain, and reperfusion injury of the brain, v) Inflammatory disorders such as psoriatic arthritis, rheumatoid arthritis, ankylosing spondylitis, osteoarthritis, inflammation and cytokine-mediated chronic tissue degeneration, vi) Allergic disorders such as allergic rhinitis, allergic conjunctivitis, and eosinophilic granuloma, vii) Psychiatric disorders such as depression, memory impairment, and monopolar depression, viii) Neurodegenerative disorders such as Parkinson disease, Alzheimer's disease, acute and chronic multiple sclerosis, ix) Dermatological disorders such as psoriasis and other benign or malignant proliferative skin diseases, atopic dermatitis, and urticaria, x) Oncological diseases such as cancer, tumor growth and cancerous invasion of normal tissues, xi) Metabolic disorders such as diabetes insipidus, xii) Bone disorders such as osteoporosis, xiii) Cardiovascular disorders such as arterial restenosis, atherosclerosis, reperfusion injury of the myocardium, and xiv) Other disorders such as chronic glomerulonephritis, vernal conjunctivitis, transplant rejection and graft versus host disease, and cachexia—maladies that are amenable to amelioration through inhibition of the PDE4 isoenzyme and the resulting elevated cAMP levels—by the administration of an effective amount of the novel alkyne-aryl substituted 1,8-naphthyridin-4(1H)-ones or a precursor compound which forms in vivo the novel alkyne-aryl substituted 1,8-naphthyridin-4(1H)-ones which are phosphodiesterase-4 inhibitors.

DETAILED DESCRIPTION OF THE INVENTION

A compound of this invention is represented by Formula (I):

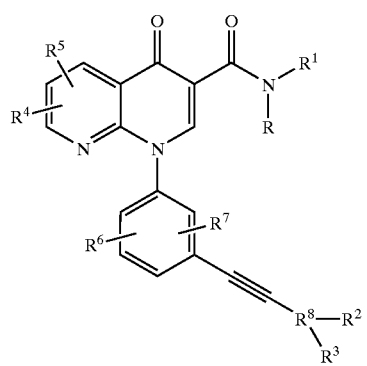

(I)

or a pharmaceutically acceptable salt thereof, wherein

R is H, —$C_{1-6}$alkyl or —$C_{3-6}$cycloalkyl;

$R^1$ is H, or a —$C_{1-6}$alkyl, —$C_{3-6}$cycloalkyl, —$C_{1-6}$alkoxy, —$C_{2-6}$alkenyl, —$C_{3-6}$alkynyl, —C(O)—$C_{1-6}$alkyl, —C(O)-aryl, —($C_{0-6}$alkyl)—$SO_n$—($C_{1-6}$alkyl), —($C_{0-6}$alkyl)$SO_n$—(aryl), phenyl, heteroaryl, or heterocyclo$C_{3-7}$alkyl group, wherein any of the groups is optionally substituted with 1–3 independent —$C_{1-6}$alkyl, —$C_{1-6}$alkoxy, OH, —N(CO6alkyl)(CO6alkyl), —($C_{0-6}$alkyl)$SO_n$—($C_{1-6}$alkyl), nitro, CN, =NO—$C_{1-6}$alkyl, —O—N=$C_{1-6}$alkyl, or halogen substituents;

$R^2$ is absent, H, halogen, —$C_{1-6}$alkyl, —$C_{3-6}$cycloalkyl, —$C_{1-6}$alkyl($C_{3-6}$cycloalkyl)($C_{3-6}$cycloalkyl), —$C_{1-6}$alkoxy, phenyl, heteroaryl, heterocyclo$C_{3-7}$alkyl, nitro, CN, =N—O—$C_{1-6}$alkyl, —O—N=$C_{1-6}$alkyl, —N($C_{0-6}$alkyl)($C_{0-6}$alkyl), —NHSO$_n$—($C_{1-6}$alkyl), —NHC(O)$C_{1-6}$alkyl, —NHC(O)-aryl, —C(O)—$C_{1-6}$alkyl, —C(O)—O—$C_{1-6}$alkyl, —$C_{1-6}$alkyl(=N—OH), —C(N=NOH)$C_{1-6}$alkyl, —$C_{0-6}$alkyl(oxy)$C_{1-6}$alkyl-phenyl, —$SO_n$NH($C_{0-6}$alkyl), or —($C_{0-6}$alkyl)$SO_n$—($C_{1-6}$alkyl), wherein the phenyl, heteroaryl or heterocyclo$C_{3-7}$alkyl is optionally substituted with halogen, —$C_{1-6}$alkyl, —$C_{1-6}$alkoxy, hydroxy, —N($C_{0-6}$alkyl)($C_{0-6}$alkyl), or —C(O)—O—$C_{1-6}$alkyl, and any alkyl is optionally substituted with 1–6 independent halogen or —OH substituents;

n is 0, 1, or 2;

$R^3$ is absent, H, OH, —N($C_{0-6}$alkyl)($C_{0-6}$alkyl), halogen or $C_{1-6}$alkyl, wherein any alkyl is optionally substituted with 1–6 independent halogen, OH, or —N($C_{0-6}$alkyl)($C_{0-6}$alkyl) substituents;

$R^4$, $R^5$, $R^6$, and $R^7$ each independently is H, halogen, —$C_{1-6}$alkyl, —$C_{1-6}$alkoxy, —$SO_n$—($C_{1-6}$alkyl), nitro, CN, or —N($C_{0-6}$alkyl)($C_{0-6}$alkyl), and any alkyl is optionally substituted with 1–6 independent halogen or —OH substituents; and $R^8$ is phenyl, pyridyl, pyrimidyl, indolyl, quinolinyl, thienyl, pyridonyl, oxazolyl, oxadiazolyl, thiazolyl, thiadiazolyl, or imidazolyl; or oxides thereof when $R^8$ is a heteroaryl; or H, —$C_{1-6}$alkyl, or —$C_{3-6}$cycloalkyl, and any alkyl is optionally substituted with 1–6 independent halogen, —N($C_{0-6}$alkyl)($C_{0-6}$alkyl), —N($C_{3-7}$cycloalkyl)($C_{0-6}$alkyl), —N($C_{3-7}$cycloalkyl)($C_{3-7}$cycloalkyl), N-heterocyclo$C_{4-7}$alkyl, —$SO_n$—($C_{1-6}$alkyl), —$SO_n$—(aryl), or —OH substituents.

In one aspect, a compound of this invention is represented by Formula (I) or a pharmaceutically acceptable salt thereof, wherein R is H, —$C_{1-6}$alkyl or —$C_{3-6}$cycloalkyl;

$R^1$ is H, or a —$C_{1-6}$alkyl, —$C_{3-6}$cycloalkyl, —$C_{1-6}$alkoxy, —$C_{2-6}$alkenyl, —$C_{3-6}$alkynyl, —C(O)—$C_{1-6}$alkyl, —C(O)-aryl, —($C_{0-6}$alkyl)—$SO_n$—($C_{1-6}$alkyl), —($C_{0-6}$alkyl)—$SO_n$—(aryl), phenyl, heteroaryl, or heterocyclo$C_{3-7}$alkyl group, wherein any of the groups is optionally substituted with 1–3 independent —$C_{1-6}$alkyl, —$C_{1-6}$alkoxy, OH, —N($C_{0-6}$alkyl)($C_{0-6}$alkyl), —($C_{0-6}$alkyl)—$SO_n$—($C_{1-6}$alkyl), nitro, CN, =N—O—$C_{1-6}$alkyl, —O—N=$C_{1-6}$alkyl, or halogen substituents;

$R^2$ is absent;

n is 0, 1, or 2;

$R^3$ is absent;

$R^4$, $R^5$, $R^6$, and $R^7$ each independently is H, halogen, —$C_{1-6}$alkyl, —$C_{1-6}$alkoxy, —$SO_n$—($C_{1-6}$alkyl), nitro, CN, or —N($C_{0-6}$alkyl)($C_{0-6}$alkyl), and any alkyl is optionally substituted with 1–6 independent halogen or —OH substituents; and $R^8$ is H.

In a second aspect, a compound of this invention is represented by Formula (I) or a pharmaceutically acceptable salt thereof, wherein R is H, —$C_{1-6}$alkyl or —$C_{3-6}$cycloalkyl;

$R^1$ is H, or a —$C_{1-6}$alkyl, —$C_{3-6}$cycloalkyl, —$C_{1-6}$alkoxy, —$C_{2-6}$alkenyl, —$C_{3-6}$alkynyl, —C(O)—$C_{1-6}$alkyl, —C(O)-aryl, —($C_{0-6}$alkyl)-SO$_n$—($C_{1-6}$alkyl), —($C_{0-6}$alkyl$_{-SO_n}$—(aryl), phenyl, heteroaryl, or heterocyclo$C_{3-7}$alkyl group, wherein any of the groups is optionally substituted with 1–3 independent —$C_{1-6}$alkyl, —$C_{1-6}$alkoxy, OH, —N($C_{0-6}$alkyl)($C_{0-6}$alkyl), —($C_{0-6}$alkyl)—SO$_n$—($C_{1-6}$alkyl), nitro, CN, =N—O—$C_{1-6}$alkyl, —O—N=$C_{1-6}$alkyl, or halogen substituents;

$R^2$ is absent, H, halogen, —$C_{1-6}$alkyl, —$C_{3-6}$cycloalkyl, —$C_{1-6}$alkyl($C_{3-6}$cycloalkyl)($C_{3-6}$cycloalkyl), —$C_{1-6}$alkoxy, phenyl, heteroaryl, heterocyclo$C_{3-7}$alkyl, nitro, CN, =N—O—$C_{1-6}$alkyl, —O—N=$C_{1-6}$alkyl, —N($C_{0-6}$alkyl)($C_{0-6}$alkyl), —NHSO$_n$—($C_{1-6}$alkyl), —NHC(O)—$C_{1-6}$alkyl, —NHC(O)-aryl, —C(O)$C_{0-6}$alkyl, —C(O)O—$C_{1-6}$alkyl, —$C_{1-6}$alkyl(=N—OH), —C(N=NOH)$C_{1-6}$alkyl, —$C_{0-6}$alkyl(oxy)$C_{1-6}$alkyl-phenyl, —SO$_n$NH($C_{0-6}$alkyl), or —($C_{0-6}$alkyl)—SO$_n$—($C_{1-6}$alkyl), wherein the phenyl, heteroaryl or heterocyclo$C_{3-7}$alkyl is optionally substituted with halogen, —$C_{1-6}$alkyl, —$C_{1-6}$alkoxy, hydroxy, —N($C_{0-6}$alkyl)($C_{0-6}$alkyl), or —C(O)—O—$C_{0-6}$alkyl, and any alkyl is optionally substituted with 1–6 independent halogen or —OH substituents;

n is 0, 1, or 2;

$R^3$ is absent, H, OH, —N($C_{0-6}$alkyl)($C_{0-6}$alkyl), halogen or $C_{1-6}$alkyl, wherein any alkyl is optionally substituted with 1–6 independent halogen, OH, or —N($C_{0-6}$alkyl)($C_{0-6}$alkyl) substituents;

$R^4$, $R^5$, $R^6$, and $R^7$ each independently is H, halogen, —$C_{1-6}$alkyl, —$C_{1-6}$alkoxy, —SO$_n$—($C_{1-6}$alkyl), nitro, CN, or —N($C_{0-6}$alkyl)($C_{0-6}$alkyl), and any alkyl is optionally substituted with 1–6 independent halogen or —OH substituents; and $R^8$ is phenyl, pyridyl, pyrimidyl, indolyl, quinolinyl, thienyl, pyridonyl, oxazolyl, oxadiazolyl, thiazolyl, thiadiazolyl, or imidazolyl; or oxides thereof when $R^8$ is a heteroaryl.

In an embodiment of the second aspect, a compound of this invention is represented by Formula (I) or a pharmaceutically acceptable salt thereof, wherein R is H, —C 16alkyl or —$C_{3-6}$cycloalkyl;

$R^1$ is H, or a —$C_{1-6}$alkyl, —$C_{3-6}$cycloalkyl, —$C_{1-6}$alkoxy, —$C_{2-6}$alkenyl, —$C_{3-6}$alkynyl, —C(O)—$C_{1-6}$alkyl, —C(O)-aryl, —($C_{0-6}$alkyl)—SO$_n$—($C_{1-6}$alkyl), —($C_{0-6}$alkyl)—SO$_n$—(aryl), phenyl, heteroaryl, or heterocyclo$C_{3-7}$alkyl group, wherein any of the groups is optionally substituted with 1–3 independent —$C_{1-6}$alkyl, —$C_{1-6}$alkoxy, OH, —N($C_{0-6}$alkyl)($C_{0-6}$alkyl), —($C_{0-6}$alkyl)SO$_n$—($C_{1-6}$alkyl), nitro, CN, =N—O—$C_{1-6}$alkyl, —O—N=$C_{1-6}$alkyl, or halogen substituents;

$R^2$ is absent, H, halogen, —$C_{1-6}$alkyl, —$C_{3-6}$cycloalkyl, —$C_{1-6}$alkyl($C_{3-6}$cycloalkyl)($C_{3-6}$cycloalkyl), —$C_{1-6}$alkoxy, phenyl, heteroaryl, heterocyclo$C_{3-7}$alkyl, nitro, CN, =N—O—$C_{1-6}$alkyl, —O—N=$C_{1-6}$alkyl, —N($C_{0-6}$alkyl)($C_{0-6}$alkyl), —NHSO$_n$$C_{1-6}$alkyl), —NHC(O)—$C_{1-6}$alkyl, —NHC(O)-aryl, —C(O)$C_{1-6}$alkyl, —C(O)—O—$C_{1-6}$alkyl, —$C_{1-6}$alkyl(=N—OH), —C(N=NOH)$C_{1-6}$alkyl, —$C_{0-6}$alkyl(oxy)$C_{1-6}$alkyl-phenyl, —SO$_n$NH($C_{0-6}$alkyl), or —($C_{0-6}$alkyl)—SO$_n$$C_{1-6}$alkyl), wherein the phenyl, heteroaryl or heterocyclo$C_{3-7}$alkyl is optionally substituted with halogen, —$C_{1-6}$alkyl, —$C_{1-6}$alkoxy, hydroxy, —N($C_{0-6}$alkyl)($C_{0-6}$alkyl), or —C(O)—O—$C_{1-6}$alkyl, and any alkyl is optionally substituted with 1–6 independent halogen or —OH substituents;

n is 0, 1, or 2;

$R^3$ is absent, H, OH, —N($C_{0-6}$alkyl)($C_{0-6}$alkyl), halogen or $C_{1-6}$alkyl, wherein any alkyl is optionally substituted with 1–6 independent halogen, OH, or —N($C_{0-6}$alkyl)($C_{0-6}$alkyl) substituents;

$R^4$, $R^5$, $R^6$, and $R^7$ each independently is H, halogen, —$C_{1-6}$alkyl, —$C_{1-6}$alkoxy, —SO$_n$—($C_{1-6}$alkyl), nitro, CN, or —N($C_{0-6}$alkyl)($C_{0-6}$alkyl), and any alkyl is optionally substituted with 1–6 independent halogen or —OH substituents; and $R^8$ is phenyl.

In another embodiment of the second aspect, a compound of this invention is represented by Formula (I) or a pharmaceutically acceptable salt thereof, wherein R is H, —$C_{1-6}$alkyl or —$C_{3-6}$cycloalkyl;

$R^1$ is H, or a —$C_{1-6}$alkyl, —$C_{3-6}$cycloalkyl, —$C_{1-6}$alkoxy, —$C_{2-6}$alkenyl, —$C_{3-6}$alkynyl, —C(O)—$C_{1-6}$alkyl, —C(O)-aryl, —($C_{0-6}$alkyl)—SO$_n$—($C_{1-6}$alkyl), —($C_{0-6}$alkyl)—SO$_n$—(aryl), phenyl, heteroaryl, or heterocyclo$C_{3-7}$alkyl group, wherein any of the groups is optionally substituted with 1–3 independent —$C_{1-6}$alkyl, —$C_{1-6}$alkoxy, OH, —N($C_{0-6}$alkyl)($C_{0-6}$alkyl), —($C_{0-6}$alkyl)—SO$_n$$C_{1-6}$alkyl), nitro, CN, =N—O—$C_{1-6}$alkyl, —O—N=$C_{1-6}$alkyl, or halogen substituents;

$R^2$ is absent, H, halogen, —$C_{1-6}$alkyl, —$C_{3-6}$cycloalkyl, —$C_{1-6}$alkyl($C_{3-6}$cycloalkyl)($C_{3-6}$cycloalkyl), —$C_{1-6}$alkoxy, phenyl, heteroaryl, heterocyclo$C_{3-7}$alkyl, nitro, CN, =N—O—$C_{1-6}$alkyl, —O—N=$C_{1-6}$alkyl, —N($C_{0-6}$alkyl)($C_{0-6}$alkyl), —NHSO$_n$$C_{1-6}$alkyl), —NHC(O)$C_{1-6}$alkyl, —NHC(O)-aryl, —C(O)$C_{1-6}$alkyl, —C(O)—O—$C_{1-6}$alkyl, —$C_{1-6}$alkyl(=N—OH), —C(N=NOH)$C_{1-6}$alkyl, —$C_{0-6}$alkyl(oxy)$C_{1-6}$alkyl-phenyl, —SO$_n$NH($C_{0-6}$alkyl), or —($C_{0-6}$alkyl)SO$_n$$C_{1-6}$alkyl), wherein the phenyl, heteroaryl or heterocyclo$C_{3-7}$alkyl is optionally substituted with halogen, —$C_{1-6}$alkyl, —$C_{1-6}$alkoxy, hydroxy, —N($C_{0-6}$alkyl)($C_{0-6}$alkyl), or —C(O)—O—$C_{1-6}$alkyl, and any alkyl is optionally substituted with 1–6 independent halogen or —OH substituents;

n is 0, 1, or 2;

$R^3$ is absent, H, OH, —N($C_{0-6}$alkyl)($C_{0-6}$alkyl), halogen or $C_{1-6}$alkyl, wherein any alkyl is optionally substituted with 1–6 independent halogen, OH, or —N($C_{0-6}$alkyl)($C_{0-6}$alkyl) substituents;

$R^4$, $R^5$, $R^6$, and $R^7$ each independently is H, halogen, —$C_{1-6}$alkyl, —$C_{1-6}$alkoxy, —SO$_n$—($C_{1-6}$alkyl), nitro, CN, or —N($C_{0-6}$alkyl)($C_{0-6}$alkyl), and any alkyl is optionally substituted with 1–6 independent halogen or —OH substituents; and $R^8$ is pyridyl, or oxides thereof.

In yet another embodiment of the second aspect, a compound of this invention is represented by Formula (I) or a pharmaceutically acceptable salt thereof, wherein R is H, —$C_{1-6}$alkyl or —$C_{3-6}$cycloalkyl;

$R^1$ is H, or a —$C_{1-6}$alkyl, —$C_{3-6}$cycloalkyl, —$C_{1-6}$alkoxy, —$C_{2-6}$alkenyl, —$C_{3-6}$alkynyl, —C(O)—$C_{1-6}$alkyl, —C(O)-aryl, —($C_{0-6}$alkyl)—SO$_n$—($C_{1-6}$alkyl), —($C_{0-6}$alkyl)—SO$_n$—(aryl), phenyl, heteroaryl, or heterocyclo$C_{3-7}$alkyl group, wherein any of the groups is optionally substituted with 1–3 independent —$C_{1-6}$alkyl, —$C_{1-6}$alkoxy, OH, —N($C_{0-6}$alkyl)($C_{0-6}$alkyl), —($C_{0-6}$alkyl)—SO$_n$$C_{1-6}$alkyl), nitro, CN, =N—O—$C_{1-6}$alkyl, —O—N=$C_{1-6}$alkyl, or halogen substituents;

$R^2$ is absent, H, halogen, —$C_{1-6}$alkyl, —$C_{3-6}$cycloalkyl, —$C_{1-6}$alkyl($C_{3-6}$cycloalkyl)($C_{3-6}$cycloalkyl), —$C_{1-6}$alkoxy, phenyl, heteroaryl, heterocyclo$C_{3-7}$alkyl, nitro, CN, =N—O—$C_{1-6}$alkyl, —O—N=$C_{1-6}$alkyl, —N($C_{0-6}$alkyl)($C_{0-6}$alkyl), —NHSO$_n$—($C_{1-6}$alkyl), —NHC(O)$C_{1-6}$alkyl, —NHC(O)-aryl, —C(O)—$C_{1-6}$alkyl, —C(O)—O—$C_{1-6}$alkyl, —$C_{1-6}$alkyl(=N—OH), —C(N=NOH)$C_{1-6}$alkyl, —$C_{0-6}$alkyl(oxy)$C_{1-6}$alkyl-phenyl, —SO$_n$NH($C_{0-6}$alkyl), or —($C_{0-6}$alkyl)—SO$_n$—($C_{1-6}$alkyl), wherein the phenyl, heteroaryl or heterocyclo$C_{3-7}$alkyl is optionally substituted with halogen, —$C_{1-6}$alkyl, —$C_{1-6}$alkoxy, hydroxy, —N($C_{0-6}$alkyl)($C_{0-6}$alkyl), or —C(O)—O—$C_{1-6}$alkyl, and any alkyl is optionally substituted with 1–6 independent halogen or —OH substituents;

n is 0, 1, or 2;

$R^3$ is absent, H, OH, —N($C_{0-6}$alkyl)($C_{0-6}$alkyl), halogen or $C_{1-6}$alkyl, wherein any alkyl is optionally substituted with 1–6 independent halogen, OH, or —N($C_{0-6}$alkyl)($C_{0-6}$alkyl) substituents;

$R^4$, $R^5$, $R^6$, and $R^7$ each independently is H, halogen, —$C_{1-6}$alkyl, —$C_{1-6}$alkoxy, —SO$_n$—($C_{1-6}$alkyl), nitro, CN, or —N($C_{0-6}$alkyl)($C_{0-6}$alkyl), and any alkyl is optionally substituted with 1–6 independent halogen or —OH substituents; and $R^8$ is quinolinyl, or oxides thereof.

In still another embodiment of the second aspect, a compound of this invention is represented by Formula (I) or a pharmaceutically acceptable salt thereof, wherein R is H, —$C_{1-6}$alkyl or —$C_{3-6}$cycloalkyl;

$R^1$ is H, or a —$C_{1-6}$alkyl, —$C_{3-6}$cycloalkyl, —$C_{1-6}$alkoxy, —$C_{2-6}$alkenyl, —$C_{3-6}$alkynyl, —C(O)—$C_{1-6}$alkyl, —C(O)-aryl, —($C_{0-6}$alkyl)SO$_n$—($C_{1-6}$alkyl), —($C_{0-6}$alkyl)—SO$_n$—(aryl), phenyl, heteroaryl, or heterocyclo$C_{3-7}$alkyl group, wherein any of the groups is optionally substituted with 1–3 independent —$C_{1-6}$alkyl, —$C_{1-6}$alkoxy, OH, —N($C_{0-6}$alkyl)($C_{0-6}$alkyl), —($C_{0-6}$alkyl)—SO$_n$—($C_{1-6}$alkyl), nitro, CN, =N—O—$C_{1-6}$alkyl, —O—N=$C_{1-6}$alkyl, or halogen substituents;

$R^2$ is absent, H, halogen, —$C_{1-6}$alkyl, —$C_{3-6}$cycloalkyl, —$C_{1-6}$alkyl($C_{3-6}$cycloalkyl)($C_{3-6}$cycloalkyl), —$C_{1-6}$alkoxy, phenyl, heteroaryl, heterocyclo$C_{3-7}$alkyl, nitro, CN, =N—O—$C_{1-6}$alkyl, —O—N=$C_{1-6}$alkyl, —N($C_{0-6}$alkyl)($C_{0-6}$alkyl), —NHSO$_n$$C_{1-6}$alkyl), —NHC(O)—$C_{1-6}$alkyl, —NHC(O)-aryl, —C(O)—$C_{1-6}$alkyl, —C(O)—O—$C_{1-6}$alkyl, —$C_{1-6}$alkyl(=N—OH), —C(N=NOH)$C_{1-6}$alkyl, —$C_{0-6}$alkyl(oxy)$C_{1-6}$alkyl-phenyl, —SO$_n$NH($C_{0-6}$alkyl), or —($C_{0-6}$alkyl)SO$_n$$C_{1-6}$alkyl), wherein the phenyl, heteroaryl or heterocyclo$C_{3-7}$alkyl is optionally substituted with halogen, —$C_{1-6}$alkyl, —$C_{1-6}$alkoxy, hydroxy, —N($C_{0-6}$alkyl)($C_{0-6}$alkyl), or —C(O)—O—$C_{1-6}$alkyl, and any alkyl is optionally substituted with 1–6 independent halogen or H substituents;

n is 0, 1, or 2;

$R^3$ is absent, H, OH, —N($C_{0-6}$alkyl)($C_{0-6}$alkyl), halogen or $C_{1-6}$alkyl, wherein any alkyl is optionally substituted with 1–6 independent halogen, OH, or —N($C_{0-6}$alkyl)($C_{0-6}$alkyl) substituents;

$R^4$, $R^5$, $R^6$, and $R^7$ each independently is H, halogen, —$C_{1-6}$alkyl, —$C_{1-6}$alkoxy, —SO$_n$—($C_{1-6}$alkyl), nitro, CN, or —N($C_{0-6}$alkyl)($C_{0-6}$alkyl), and any alkyl is optionally substituted with 1–6 independent halogen or —OH substituents; and $R^8$ is thienyl, or oxides thereof.

In another embodiment of the second aspect, a compound of this invention is represented by Formula (I) or a pharmaceutically acceptable salt thereof, wherein R is H, —$C_{1-6}$alkyl or —$C_{3-6}$cycloalkyl;

$R^1$ is H, or a —$C_{1-6}$alkyl, —$C_{3-6}$cycloalkyl, —$C_{1-6}$alkoxy, —$C_{2-6}$alkenyl, —$C_{3-6}$alkynyl, —C(O)—$C_{1-6}$alkyl, —C(O)-aryl, —($C_{0-6}$alkyl)—SO$_n$$C_{1-6}$alkyl), —($C_{0-6}$alkyl)—SO$_n$aryl), phenyl, heteroaryl, or heterocyclo$C_{3-7}$alkyl group, wherein any of the groups is optionally substituted with 1–3 independent —$C_{1-6}$alkyl, —$C_{1-6}$alkoxy, OH, —N($C_{0-6}$alkyl)($C_{0-6}$alkyl), —($C_{0-6}$alkyl)—SO$_n$—($C_{1-6}$alkyl), nitro, CN, =N—O—$C_{1-6}$alkyl, —O—N=$C_{1-6}$alkyl, or halogen substituents;

$R^2$ is absent, H, halogen, —$C_{1-6}$alkyl, —$C_{3-6}$cycloalkyl, —$C_{1-6}$alkyl($C_{3-6}$cycloalkyl)($C_{3-6}$cycloalkyl), —$C_{1-6}$alkoxy, phenyl, heteroaryl, heterocyclo$C_{3-7}$alkyl, nitro, CN, =N—O—$C_{1-6}$alkyl, —O—N=$C_{1-6}$alkyl, —N($C_{0-6}$alkyl)($C_{0-6}$alkyl), —NHSO$_n$—($C_{1-6}$alkyl), —NHC(O)$C_{1-6}$alkyl, —NHC(O)-aryl, —C(O)$C_{1-6}$alkyl, —C(O)O—$C_{1-6}$alkyl, —$C_{1-6}$alkyl(=N—OH), —C(N=NOH)$C_{1-6}$alkyl, —$C_{0-6}$alkyl(oxy)$C_{1-6}$alkyl-phenyl, —SO$_n$NH($C_{0-6}$alkyl), or —($C_{0-6}$alkyl)—SO$_n$—($C_{1-6}$alkyl), wherein the phenyl, heteroaryl or heterocyclo$C_{3-7}$alkyl is optionally substituted with halogen, —$C_{1-6}$alkyl, —$C_{1-6}$alkoxy, hydroxy, —N($C_{0-6}$alkyl)($C_{0-6}$alkyl), or —C(O)-O—$C_{1-6}$alkyl, and any alkyl is optionally substituted with 1–6 independent halogen or —OH substituents;

n is 0, 1, or 2;

$R^3$ is absent, H, OH, —N($C_{0-6}$alkyl)($C_{0-6}$alkyl), halogen or $C_{1-6}$alkyl, wherein any alkyl is optionally substituted with 1–6 independent halogen, OH, or —N($C_{0-6}$alkyl)($C_{0-6}$alkyl) substituents;

$R^4$, $R^5$, $R^6$, and $R^7$ each independently is H, halogen, —$C_{1-6}$alkyl, —$C_{1-6}$alkoxy, —SO$_n$—($C_{1-6}$alkyl), nitro, CN, or —N($C_{0-6}$alkyl)($C_{0-6}$alkyl), and any alkyl is optionally substituted with 1–6 independent halogen or H substituents; and $R^8$ is thiazolyl, or oxides thereof.

In a third aspect, a compound of this invention is represented by Formula (1) or a pharmaceutically acceptable salt thereof, wherein R is H, —$C_{1-6}$alkyl or —$C_{3-6}$cycloalkyl;

$R^1$ is H, or a —$C_{1-6}$alkyl, —$C_{3-6}$cycloalkyl, —$C_{1-6}$alkoxy, —$C_{2-6}$alkenyl, —$C_{3-6}$alkynyl, —C(O)—$C_{1-6}$alkyl, —C(O)-aryl, —($C_{0-6}$alkyl)SO$_n$—($C_{1-6}$alkyl), —($C_{0-6}$alkyl)—SO$_n$—(aryl), phenyl, heteroaryl, or heterocyclo$C_{3-7}$alkyl group, wherein any of the groups is optionally substituted with 1–3 independent —$C_{1-6}$alkyl, —$C_{1-6}$alkoxy, OH, —N($C_{0-6}$alkyl)($C_{0-6}$alkyl), —($C_{0-6}$alkyl)—SO$_n$—($C_{1-6}$alkyl), nitro, CN, =N—O—$C_{1-6}$alkyl, —O—N=$C_{1-6}$alkyl, or halogen substituents;

$R^2$ is absent, H, halogen, —$C_{1-6}$alkyl, —$C_{3-6}$cycloalkyl, —$C_{1-6}$alkyl($C_{3-6}$cycloalkyl)($C_{3-6}$cycloalkyl), —$C_{1-6}$alkoxy, phenyl, heteroaryl, heterocyclo$C_{3-7}$alkyl, nitro, CN, =N—O—$C_{1-6}$alkyl, —O—N=$C_{1-6}$alkyl, —N($C_{0-6}$alkyl)($C_{0-6}$alkyl), —NHSO$_n$—($C_{1-6}$alkyl), —NHC(O)—$C_{1-6}$alkyl, —NHC(O)-aryl, —C(O)—$C_{1-6}$alkyl, —C(O)—O—$C_{1-6}$alkyl, —$C_{1-6}$alkyl(=N—OH), —C(N=NOH)$C_{1-6}$alkyl, —$C_{0-6}$alkyl(oxy)$C_{1-6}$alkyl-phenyl, —SO$_n$NH($C_{0-6}$alkyl), or —($C_{0-6}$alkyl)SO$_n$—($C_{1-6}$alkyl), wherein the phenyl, heteroaryl or heterocycloC$_{3-7}$alkyl is optionally substituted with halogen, —C$_{1-6}$alkyl, —C$_{1-6}$alkoxy, hydroxy, —N(C$_{0-6}$alkyl)(C$_{0-6}$alkyl), or —C(O)—O—C$_{1-6}$alkyl, and any alkyl is optionally substituted with 1–6 independent halogen or —OH substituents;

n is 0, 1, or 2;

R$^3$ is absent, H, OH, —N(C$_{0-6}$alkyl)(C$_{0-6}$alkyl), halogen or C$_{1-6}$alkyl, wherein any alkyl is optionally substituted with 1–6 independent halogen, OH, or —N(C$_{0-6}$alkyl)(C$_{0-6}$alkyl) substituents;

R$^4$, R$^5$, R$^6$, and R$^7$ each independently is H, halogen, —C$_{1-6}$alkyl, —C$_{1-6}$alkoxy, —SO$_n$—(C$_{1-6}$alkyl), nitro, CN, or —N(C$_{0-6}$alkyl)(C$_{0-6}$alkyl), and any alkyl is optionally substituted with 1–6 independent halogen or H substituents; and R$^8$ is —C$_{3-6}$cycloalkyl, optionally substituted with 1–6 independent halogen, —N(C$_{0-6}$alkyl)(C$_{0-6}$alkyl), —N(C$_{3-7}$cycloalkyl)(C$_{0-6}$alkyl), —N(C$_{3-7}$cycloalkyl)(C$_{3-7}$cycloalkyl), N-heterocycloC$_{4-7}$alkyl, —SO$_n$—(C$_{1-6}$alkyl), —SO$_n$—(aryl), or H substituents.

In a fourth aspect, a compound of this invention is represented by Formula (I) or a pharmaceutically acceptable salt thereof, wherein R is H, —C$_{1-6}$alkyl or —C$_{3-6}$cycloalkyl;

R$^1$ is H, or a —C$_{1-6}$alkyl, —C$_{3-6}$cycloalkyl, —C$_{1-6}$alkoxy, —C$_{2-6}$alkenyl, —C$_{3-6}$alkynyl, —C(O)—C$_{1-6}$alkyl, —C(O)-aryl, —(C$_{0-6}$alkyl)—SO$_n$—(C$_{1-6}$alkyl), —(C$_{0-6}$alkyl)SO$_n$—(aryl), phenyl, heteroaryl, or heterocycloC$_{3-7}$alkyl group, wherein any of the groups is optionally substituted with 1–3 independent —C$_{1-6}$alkyl, —C$_{1-6}$alkoxy, OH, —N(C$_{0-6}$alkyl)(C$_{0-6}$alkyl), —(C$_{0-6}$alkyl)—SO$_n$—(C$_{1-6}$alkyl), nitro, CN, =N—O—C$_{1-6}$alkyl, —O—N=C$_{1-6}$alkyl, or halogen substituents;

R$^2$ is absent, H, halogen, —C$_{1-6}$alkyl, —C$_{3-6}$cycloalkyl, —C$_{1-6}$alkyl(C$_{3-6}$cycloalkyl)(C$_{3-6}$cycloalkyl), —C$_{1-6}$alkoxy, phenyl, heteroaryl, heterocycloC$_{3-7}$alkyl, nitro, CN, =N—O—C$_{1-6}$alkyl, —O—N=C$_{1-6}$alkyl, —N(C$_{0-6}$alkyl)(C$_{0-6}$alkyl), —NHSO$_n$—(C$_{1-6}$alkyl), —NHC(O)—C$_{1-6}$alkyl, —NHC(O)-aryl, —C(O)—C$_{1-6}$alkyl, —C(O)—O—C$_{1-6}$alkyl, —C$_{1-6}$alkyl(=N—OH), —C(N=NOH)C$_{1-6}$alkyl, —C$_{0-6}$alkyl(oxy)C$_{1-6}$alkyl-phenyl, —SO$_n$NH(C$_{0-6}$alkyl), or —(C$_{0-6}$alkyl)SO$_n$C$_{1-6}$alkyl), wherein the phenyl, heteroaryl or heterocycloC$_{3-7}$alkyl is optionally substituted with halogen, —C$_{1-6}$alkyl, —C$_{1-6}$alkoxy, hydroxy, —N(C$_{0-6}$alkyl)(C$_{0-6}$alkyl), or —C(O)—O—C$_{1-6}$alkyl, and any alkyl is optionally substituted with 1–6 independent halogen or —OH substituents;

n is 0, 1, or 2;

R$^3$ is absent, H, OH, —N(C$_{0-6}$alkyl)(C$_{0-6}$alkyl), halogen or C$_{1-6}$alkyl, wherein any alkyl is optionally substituted with 1–6 independent halogen, OH, or —N(C$_{0-6}$alkyl)(C$_{0-6}$alkyl) substituents;

R$^4$, R$^5$, R$^6$, and R$^7$ each independently is H, halogen, —C$_{1-6}$alkyl, —C$_{1-6}$alkoxy, —SO$_n$—(C$_{1-6}$alkyl), nitro, CN, or —N(C$_{0-6}$alkyl)(C$_{0-6}$alkyl), and any alkyl is optionally substituted with 1–6 independent halogen or —OH substituents; and R$^8$ is —C$_{1-6}$alkyl, optionally substituted with 1–6 independent halogen, —N(C$_{0-6}$alkyl)(C$_{0-6}$alkyl), —N(C$_{3-7}$cycloalkyl)(C$_{0-6}$alkyl), —N(C$_{3-7}$cycloalkyl)(C$_{3-7}$cycloalkyl), N-heterocycloC$_{4-7}$alkyl, —SO$_n$—(C$_{1-6}$alkyl), —SO$_n$—(aryl), or —OH substituents.

As used herein, "alkyl" as well as other groups having the prefix "alk" such as, for example, alkoxy, alkanoyl, alkenyl, alkynyl and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains containing at least one unsaturated C-C bond.

The term "cycloalkyl" means carbocycles containing no heteroatoms, and includes mono-, bi- and tricyclic saturated carbocycles, as well as fused ring systems. Such fused ring systems can include one ring that is partially or fully unsaturated such as a benzene ring to form fused ring systems such as benzofused carbocycles. Cycloalkyl includes such fused ring systems as spirofused ring systems. Examples of cycloalkyl include cyclopropyl, cyclobutyl, cyclopentyl, cyclohexyl, decahydronaphthalenyl, adamantanyl, indanyl, indenyl, fluorenyl, 1,2,3,4-tetrahydronaphthalenyl and the like. Similarly, "cycloalkenyl" means carbocycles containing no heteroatoms and at least one non-aromatic C-C double bond, and include mono-, bi- and tricyclic partially saturated carbocycles, as well as benzofused cycloalkenes. Examples of cycloalkenyl include cyclohexenyl, indenyl, and the like.

The term "cycloalkyloxy" unless specifically stated otherwise includes a cycloalkyl group connected to the oxy connecting atom.

The term "alkoxy" unless specifically stated otherwise includes an alkyl group connected to the oxy connecting atom.

The term "aryl" unless specifically stated otherwise includes multiple ring systems as well as single ring systems such as, for example, phenyl or naphthyl.

The term "aryloxy" unless specifically stated otherwise includes multiple ring systems as well as single ring systems such as, for example, phenyl or naphthyl, connected through the oxy connecting atom to the connecting site.

The term "C$_{0-6}$alkyl" includes alkyls containing 6, 5, 4, 3, 2, 1, or no carbon atoms. An alkyl with no carbon atoms is a hydrogen atom substituent when the alkyl is a terminus moiety. An alkyl with no carbon atoms is a direct bond when the alkyl is a bridging moiety.

The term "hetero" unless specifically stated otherwise includes one or more O, S, or N atoms. For example, heterocycloalkyl and heteroaryl include ring systems that contain one or more O, S, or N atoms in the ring, including mixtures of such atoms. The heteroatoms replace ring carbon atoms. Thus, for example, a heterocycloC$_5$alkyl is a five membered ring containing from 5 to no carbon atoms.

Examples of heteroaryl include, for example, pyridinyl, quinolinyl, isoquinolinyl, pyridazinyl, pyrimidinyl, pyrazinyl, quinoxalinyl, furyl, benzofuryl, dibenzofuryl, thienyl, benzothienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl, tetrazolyl.

The term "heteroaryloxy" unless specifically stated otherwise describes a heteroaryl group connected through an oxy connecting atom to the connecting site.

Examples of heteroaryl(C$_{1-6}$)alkyl include, for example, furylmethyl, furylethyl, thienylmethyl, thienylethyl, pyrazolylmethyl, oxazolylmethyl, oxazolylethyl, isoxazolylmethyl, thiazolylmethyl, thiazolylethyl, imidazolylmethyl, imidazolylethyl, benzimidazolylmethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyridazinylmethyl, pyrimidinylmethyl, pyrazinylmethyl, quinolinylmethyl, isoquinolinylmethyl and quinoxalinylmethyl.

Examples of heterocyclo$C_{3-7}$alkyl include, for example, azetidinyl, pyrrolidinyl, piperidinyl, perhydroazepinyl, piperazinyl, morpholinyl, tetrahydrofuranyl, imidazolinyl, pyrolidin-2-one, piperidin-2-one, and thiomorpholinyl.

The term "N-heterocyclo$C_{4-7}$alkyl" describes nonaryl heterocyclic compounds having 3–6 carbon atoms and one nitrogen atom forming the ring. Examples include azetidinyl, pyrrolidinyl, piperidinyl, and perhydroazepinyl.

Examples of aryl($C_{1-6}$)alkyl include, for example, phenyl ($C_{1-6}$)alkyl, and naphthyl($C_{1-6}$)alkyl.

Examples of heterocyclo$C_{3-7}$alkylcarbonyl($C_{1-6}$)alkyl include, for example, azetidinyl carbonyl($C_{1-6}$)alkyl, pyrrolidinyl carbonyl($C_{1-6}$)alkyl, piperidinyl carbonyl($C_{1-6}$)alkyl, piperazinyl carbonyl($C_{1-6}$)alkyl, morpholinyl carbonyl ($C_{1-6}$)alkyl, and thiomorpholinyl carbonyl($C_{1-6}$)alkyl.

The term "amine" unless specifically stated otherwise includes primary, secondary and tertiary amines.

Unless otherwise stated, the term "carbamoyl" is used to include —NHC(O)O$C_{1-4}$alkyl, and —OC(O)NH$C_{1-4}$alkyl.

The term "halogen" includes fluorine, chlorine, bromine and iodine atoms.

The term "optionally substituted" is intended to include both substituted and unsubstituted. Thus, for example, optionally substituted aryl could represent a pentafluorophenyl or a phenyl ring. Further, the substitution can be made at any of the groups. For example, substituted aryl($C_{1-6}$) alkyl includes substitution on the aryl group as well as substitution on the alkyl group.

The term "oxide" of heteroaryl groups is used in the ordinary well-known chemical sense and include, for example, N-oxides of nitrogen heteroatoms.

Compounds described herein contain one or more double bonds and may thus give rise to cis/trans isomers as well as other conformational isomers. The present invention includes all such possible isomers as well as mixtures of such isomers.

Compounds described herein can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included.

During the course of the synthetic procedures used to prepare such compounds, or in using racemization or epimerization procedures known to those skilled in the art, the products of such procedures can be mixtures of stereoisomers.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are benzenesulfonic, citric, hydrobromic, hydrochloric, maleic, phosphoric, sulfuric, and tartaric acids.

The pharmaceutical compositions of the present invention comprise a compound represented by Formula I (or pharmaceutically acceptable salts thereof) as an active ingredient, a pharmaceutically acceptable carrier and optionally other therapeutic ingredients or adjuvants. Such additional therapeutic ingredients include, for example, i) Leukotriene receptor antagonists, ii) Leukotriene biosynthesis inhibitors, iii) corticosteroids, iv) H1 receptor antagonists, v) beta 2 adrenoceptor agonists, vi) COX-2 selective inhibitors, vii) statins, viii) non-steroidal anti-inflammatory drugs ("NSAID"), and ix) M2/M3 antagonists. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

Creams, ointments, jellies, solutions, or suspensions containing the compound of Formula I can be employed for topical use. Mouth washes and gargles are included within the scope of topical use for the purposes of this invention.

Dosage levels from about 0.001mg/kg to about 140mg/kg of body weight per day are useful in the treatment of conditions such as i) Pulmonary disorders such as asthma, chronic bronchitis, chronic obstructive pulmonary disease (COPD), adult respiratory distress syndrome, infant respiratory distress syndrome, cough, chronic obstructive pulmonary disease in animals, adult respiratory distress syndrome, and infant respiratory distress syndrome, ii) Gastrointestinal disorders such as ulcerative colitis, Crohn's disease, and hypersecretion of gastric acid, iii) Infectious diseases such as bacterial, fungal or viral induced sepsis or septic shock, endotoxic shock (and associated conditions such as laminitis and colic in horses), and septic shock, iv) Neurological disorders such as spinal cord trauma, head injury, neurogenic inflammation, pain, and reperfusion injury of the brain, v) Inflammatory disorders such as psoriatic arthritis, rheumatoid arthritis, ankylosing spondylitis, osteoarthritis, inflammation and cytokine-mediated chronic tissue degeneration, vi) Allergic disorders such as allergic rhinitis, allergic conjunctivitis, and eosinophilic granuloma, vii) Psychiatric disorders such as depression, memory impairment, and monopolar depression, viii) Neurodegenerative disorders such as Parkinson disease, Alzheimer's disease, acute and chronic multiple sclerosis, ix) Dermatological disorders such as psoriasis and other benign or malignant proliferative skin diseases, atopic dermatitis, and urticaria, x) Oncological diseases such as cancer, tumor growth and cancerous invasion of normal tissues, xi) Metabolic disorders such as diabetes insipidus, xii) Bone disorders such as osteoporosis, xiii) Cardiovascular disorders such as arterial restenosis, atherosclerosis, reperfusion injury of the myocardium, and xiv) Other disorders such as chronic glomerulonephritis, vernal conjunctivitis, transplant rejection and graft versus host disease, and cachexia—which are responsive to PDE4 inhibition, or alternatively about 0.05 mg to about 7 g per patient per day. For example, inflammation may be effectively treated by the administration of from about 0.01 mg to 50 mg of the compound per kilogram of body weight per day, or alternatively about 0.5 mg to about 2.5 g per patient per day. Further, it is understood that the PDE4 inhibiting compounds of this invention can be administered at prophylactically effective dosage levels to prevent the above-recited conditions.

The amount of active ingredient that may be combined with the carrier materials to produce a single dosage form will vary depending upon the host treated and the particular mode of administration. For example, a formulation intended for the oral administration to humans may conveniently contain from about 0.5 mg to about 5 g of active agent, compounded with an appropriate and convenient amount of carrier material which may vary from about 5 to about 95 percent of the total composition. Unit dosage forms will generally contain between from about 0.01 mg to about 1000 mg of the active ingredient, typically 0.01 mg, 0.05 mg, 0.25 mg, 1 mg, 5 mg, 25 mg, 50 mg, 100 mg, 200 mg, 300 mg, 400 mg, 500 mg, 600 mg, 800 mg or 1000 mg.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

In practice, the compounds represented by Formula I, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compound represented by Formula I, or pharmaceutically acceptable salts thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

The compounds and pharmaceutical compositions of this invention have been found to exhibit biological activity as PDE4 inhibitors. Accordingly, another aspect of the invention is the treatment in mammals of, for example, i) Pulmonary disorders such as asthma, chronic bronchitis, chronic obstructive pulmonary disease (COPD), adult respiratory distress syndrome, infant respiratory distress syndrome, cough, chronic obstructive pulmonary disease in animals, adult respiratory distress syndrome, and infant respiratory distress syndrome, ii) Gastrointestinal disorders such as ulcerative colitis, Crohn's disease, and hypersecretion of gastric acid, iii) Infectious diseases such as bacterial, fungal or viral induced sepsis or septic shock, endotoxic shock (and associated conditions such as laminitis and colic in horses), and septic shock, iv) Neurological disorders such as spinal cord trauma, head injury, neurogenic inflammation, pain, and reperfusion injury of the brain, v) Inflammatory disorders such as psoriatic arthritis, rheumatoid arthritis, ankylosing spondylitis, osteoarthritis, inflammation and cytokine-mediated chronic tissue degeneration, vi) Allergic disorders such as allergic rhinitis, allergic conjunctivitis, and eosinophilic granuloma, vii) Psychiatric disorders such as depression, memory impairment, and monopolar depression, viii) Neurodegenerative disorders such as Parkinson disease, Alzheimer's disease, acute and chronic multiple sclerosis, ix) Dermatological disorders such as psoriasis and other benign or malignant proliferative skin diseases, atopic dermatitis, and urticaria, x) Oncological diseases such as cancer, tumor growth and cancerous invasion of normal tissues, xi) Metabolic disorders such as diabetes insipidus, xii) Bone disorders such as osteoporosis, xiii) Cardiovascular disorders such as arterial restenosis, atherosclerosis, reperfusion injury of the myocardium, and xiv) Other disorders such as chronic glomerulonephritis, vernal conjunctivitis, transplant rejection and graft versus host disease, and cachexia—maladies that are amenable to amelioration through inhibition of the PDE4 isoenzyme and the resulting elevated cAMP levels—by the administration of an effective amount of the compounds of this invention. The term "mammals" includes humans, as well as other animals such as, for example, dogs, cats, horses, pigs, and cattle. Accordingly, it is understood that the treatment of mammals other than humans is the treatment of clinical correlating afflictions to those above recited examples that are human afflictions.

Further, as described above, the compound of this invention can be utilized in combination with other therapeutic compounds. In particular, the combinations of the PDE4 inhibiting compound of this invention can be advantageously used in combination with i) Leukotriene receptor antagonists, ii) Leukotriene biosynthesis inhibitors, iii) COX-2 selective inhibitors, iv) statins, v) NSAIDs, vi) M2/M3 antagonists, vii) corticosteroids, viii) H1 (histamine) receptor antagonists and ix) beta 2 adrenoceptor agonist.

Thus, for example, pulmonary disorders such as asthma, chronic bronchitis, chronic obstructive pulmonary disease (COPD), adult respiratory distress syndrome, infant respiratory distress syndrome, cough, chronic obstructive pulmonary disease in animals, adult respiratory distress syndrome, and infant respiratory distress syndrome can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

Gastrointestinal disorders such as ulcerative colitis, Crohn's disease, and hypersecretion of gastric acid can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

Infectious diseases such as bacterial, fungal or viral induced sepsis or septic shock, endotoxic shock (and associated conditions such as laminitis and colic in horses), and septic shock can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

Neurological disorders such as spinal cord trauma, head injury, neurogenic inflammation, pain, and reperfusion injury of the brain can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

Inflammatory disorders such as psoriatic arthritis, rheumatoid arthritis, ankylosing spondylitis, osteoarthritis, inflammation and cytokine-mediated chronic tissue degeneration can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

Allergic disorders such as allergic rhinitis, allergic conjunctivitis, and eosinophilic granuloma can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

Psychiatric disorders such as depression, memory impairment, and monopolar depression can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

Neurodegenerative disorders such as Parkinson disease, Alzheimer's disease, acute and chronic multiple sclerosis can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

Dermatological disorders such as psoriasis and other benign or malignant proliferative skin diseases, atopic dermatitis, and urticaria can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

Oncological diseases such as cancer, tumor growth and cancerous invasion of normal tissues can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

Metabolic disorders such as diabetes insipidus can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

Bone disorders such as osteoporosis, cardiovascular disorders such as arterial restenosis, atherosclerosis, reperfusion injury of the myocardium, and other disorders such as chronic glomerulonephritis, vernal conjunctivitis, transplant rejection and graft versus host disease, and cachexia can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

The abbreviations used herein have the following tabulated meanings. Abbreviations not tabulated below have their meanings as commonly used unless specifically stated otherwise.

Ac = acetyl
Bn = benzyl
CAMP cyclic adenosine-3',5'-monophosphate
DBU = 1,8-diazabicyclo[5.4.0]undec-7-ene
DIBAL = diisobutylaluminum hydride -continued DMAP = 4-(dimethylamino)pyridine
DMF = N,N-dimethylformamide
$Et_3N$ = triethylamine
GST glutathione transferase
HMDS hexamethyldisilazide
LDA = lithium diisopropylamide
m-CPBA = metachloroperbenzoic acid
MMPP = monoperoxyphthalic acid
MPPM = monoperoxyphthalic acid, magnesium salt $6H_2O$
Ms = methanesulfonyl = mesyl = $SO_2Me$
MsO = methanesulfonate = mesylate
NSAID = non-steroidal anti-inflammatory drug
o-Tol = ortho-tolyl
OXONE ® = $2KHSO_5.KHSO_4.K_2SO_4$
PCC = pyridinium chlorochromate
PDC = pyridinium dichromate
PDE phosphodiesterase
Ph = phenyl
Phe = benzenediyl
PMB = para-methoxybenzyl
Pye = pyridinediyl
r.t. = room temperature
Rac. = racemic
SAM = aminosulfonyl or sulfonamide or $SO_2NH_2$
SEM = 2-(trimethylsilyl)ethoxymethoxy
SPA = scintillation proximity assay
TBAF = tetra-n-butylammonium fluoride
Th = 2- or 3-thienyl
TFA = trifluoroacetic acid
TFAA = trifluoroacetic acid anhydride
THF = tetrahydrofuran
Thi = thiophenediyl
TLC = thin layer chromatography
TMS-CN = trimethylsilyl cyanide
TMSI trimethylsilyl iodide
Tz = 1H (or 2H)-tetrazol-5-yl
CAN ceric ammonium nitrate
$C_3H_5$ = allyl

ALKYL GROUP ABBREVIATIONS

Me = Methyl
Et = ethyl
n-Pr = normal propyl
i-Pr = isopropyl
n-Bu = normal butyl
i-Bu = isobutyl
s-Bu = secondary butyl
t-Bu = tertiary butyl
c-Pr = cyclopropyl
c-Bu = Cyclobutyl
c-Pen = cyclopentyl
c-Hex = cyclohexyl Assays Demonstrating Biological Activity LPS and FMLP-induced TNF-α and $LTB_4$ Assays in Human Whole Blood Whole blood provides a protein and cell-rich milieu appropriate for the study of biochemical efficacy of anti-inflammatory compounds such as PDE4-selective inhibitors. Normal non-stimulated human blood does not contain detectable levels of TNF-α and LTB4. Upon stimulation with LPS, activated monocytes express and secrete TNF-α up to 8 hours and plasma levels remain stable for 24 hours. Published studies have shown that inhibition of TNF-α by increasing intracellular cAMP via PDE4 inhibition and/or enhanced adenylyl cyclase activity occurs at the transcriptional level. LTB4 synthesis is also sensitive to levels of intracellular cAMP and can be completely inhibited by PDE4-selective inhibitors. As there is little LTB4 produced during a 24 hour LPS stimulation of whole blood, an additional LPS stimulation followed by fMLP challenge of human whole blood is necessary for LTB4 synthesis by activated neutrophils. Thus, by using the same blood sample, it is possible to evaluate the potency of a compound on two surrogate markers of PDE4 activity in the whole blood by the following procedure.

Fresh blood was collected in heparinized tubes by venipuncture from healthy human volunteers (male and female). These subjects had no apparent inflammatory conditions and had not taken any NSAIDs for at least 4 days prior to blood collection. 500 µL aliquots of blood were pre-incubated with either 2 µL of vehicle (DMSO) or 2 µL of test compound at varying concentrations for 15 minutes at 37° C. This was followed by the addition of either 10 µL vehicle (PBS) as blanks or 10 µL LPS (1 µg/mL final concentration, #L-2630 (Sigma Chemical Co., St. Louis, Mo.) from $E.\ coli$, serotype 0111:B4; diluted in 0.1% w/v BSA (in PBS)). After 24 hours of incubation at 37° C., another 10 µL of PBS (blank) or 10 µL of LPS (1 µg/mL final concentration) was added to blood and incubated for 30 minutes at 37° C. The blood was then challenged with either 10 µL of PBS (blank) or 10 µL of fMLP (1 µM final concentration, #F-3506 (Sigma); diluted in 1% w/v BSA (in PBS)) for 15 minutes at 37° C. The blood samples were centrifuged at 1500×g for 10 minutes at 4° C. to obtain plasma. A 50 µL aliquot of plasma was mixed with 200 µL methanol for protein precipitation and centrifuged as above. The supernatant was assayed for LTB4 using an enzyme immunoassay kit (#520111 from Cayman Chemical Co., Ann Arbor, Mich.) according to the manufacturer's procedure. TNF-α was assayed in diluted plasma (in PBS) using an ELISA kit (Cistron Biotechnology, Pine Brook, N.J.) according to manufacturer's procedure. $IC_{50}$ values should be less than about 5 µM, advantageously less than about 2.5 µM. The $IC_{50}$ values of Examples 1 to 33 ranged from 0.01 µM to 2.4 µM.

Anti-allergic Activity In Vivo

Compounds of the invention have been tested for effects on an IgE-mediated allergic pulmonary inflammation induced by inhalation of antigen by sensitized guinea pigs. Guinea pigs were initially sensitized to ovalbumin under mild cyclophosphamide-induced immunosuppression, by intraperitoneal injection of antigen in combinations with aluminum hydroxide and pertussis vaccine. Booster doses of antigen were given two and four weeks later. At six weeks, animals were challenged with aerosolized ovalbumin while under cover of an intraperitoneally administered antihistamine agent (mepyramine). After a further 48 h, bronchial alveolar lavages (BAL) were performed and the numbers of eosinophils and other leukocytes in the BAL fluids were counted. The lungs were also removed for histological examination for inflammatory damage. Administration of compounds of the Examples (0.001–10 mg/kg i.p. or p.o.), up to three times during the 48 h following antigen challenge, lead to a significant reduction in the eosinophilia and the accumulation of other inflammatory leukocytes.

SPA Based PDE Activity Assay Protocol

Compounds which inhibit the hydrolysis of cAMP to AMP by the type-IV cAMP-specific phosphodiesterases were screened in a 96-well plate format as follows:

In a 96 well-plate at 30° C. the test compound was added (dissolved in 2 µL DMSO), 188 µL of substrate buffer containing [2,8-$^3$H] adenosine 3',5'-cyclic phosphate (cAMP, 100 nM to 50 µM), 10 mM $MgCl_2$, 1 mM EDTA, 50 mM Tris, pH 7.5. The reaction was initiated by the addition of human recombinant PDE4 (the amount was controlled so that 10% product was formed in 10 min.). The reaction was stopped after 10 min. by the addition of 1 mg of PDE-SPA beads (Amersham Pharmacia Biotech, Inc., Piscataway, N.J.). The product AMP generated was quantified on a Wallac Microbeta® 96-well plate counter (EG&G Wallac Co., Gaithersburg, Md.). The signal in the absence of enzyme was defined as the background. 100% activity was defined as the signal detected in the presence of enzyme and DMSO with the background subtracted. Percentage of inhibition was calculated accordingly. $IC_{50}$ value was approximated with a non-linear regression fit using the standard 4-parameter/multiple binding sites equation from a ten point titration.

The $IC_{50}$ values of Examples 1 to 33 were determined with 100 nM cAMP using the purified GST fusion protein of the human recombinant phosphodiesterase IVa (met-248) produced from a baculovirus/Sf-9 expression system. $IC_{50}$ values should be less than about 1000 nM, advantageously less than about 250 nM, and even more advantageously less than about 100 nM. The $IC_{50}$ values of Examples 1 to 33 ranged from 0.1 nM to 90.0 nM.

The Examples that follow are intended as an illustration of certain preferred embodiments of the invention and no limitation of the invention is implied.

Unless specifically stated otherwise, the experimental procedures were performed under the following conditions. All operations were carried out at room or ambient temperature—that is, at a temperature in the range of 18–25° C. Evaporation of solvent was carried out using a rotary evaporator under reduced pressure (600–4000 pascals: 4.5–30 mm Hg) with a bath temperature of up to 60° C. The course of reactions was followed by thin layer chromatography (TLC) and reaction times are given for illustration only. Melting points are uncorrected and "d" indicates decomposition. The melting points given are those obtained for the materials prepared as described. Polymorphism may result in isolation of materials with different melting points in some preparations. The structure and purity of all final products were assured by at least one of the following techniques: TLC, mass spectrometry, nuclear magnetic resonance (NMR) spectrometry or microanalytical data. When given, yields are for illustration only. When given, NMR data is in the form of delta (δ) values for major diagnostic protons, given in parts per million (ppm) relative to tetramethylsilane (TMS) as internal standard, determined at 300 MHz, 400 MHz or 500 MHz using the indicated solvent. Conventional abbreviations used for signal shape are: s. singlet; d. doublet; t. triplet; m. multiplet; br. broad; etc. In addition, "Ar" signifies an aromatic signal. Chemical symbols have their usual meanings; the following abbreviations have also been used: v (volume), w (weight), b.p. (boiling point), m.p. (melting point), L (liter(s)),mL (milliliters), g (gram(s)), mg (milligrams(s)), mol (moles), mmol (millimoles), eq (equivalent(s)).

Methods of Synthesis

Compounds of the present invention can be prepared according to the following methods. The substituents are the same as in Formula I except where defined otherwise.

In a first method outlined below in Scheme 1, an appropriately substituted derivative of ethyl 2-chloronicotinoyl acetate of formula II is reacted with 1.5 equivalents of triethyl orthoformate and 5 equivalents of acetic anhydride at 130° C., and after removal of the volatile components the crude 2-chloronicotinoyl acrylate of formula III is immediately reacted with 1.2 equivalents of an appropriately substituted haloaryl amine of formula IV, such as, for example 3-bromoaniline, in a halogenated hydrocarbon solvent such as methylene chloride at a temperature of 0° C. to room temperature. After an appropriate reaction time ranging from 2 to 24 hours the resulting 3-arylamino acrylate of formula V is obtained by evaporation of the solvent and may be further purified by chromatography on silica gel or crystallization from an appropriate solvent. The compound of formula V may alternatively be used without further purification in the following step. Cyclization of the compound of formula V to the 1-haloaryl-1,4-dihydro[1,8]naphthyridin-4-one carboxylate of formula VI is effected by treatment with a small excess of a strong base such as an alkali metal hydride, for example sodium hydride, in an appropriate solvent such as tetrahydrofuran at a starting temperature of 0° C. with warming to room temperature if required to complete the process. The product of formula VI is isolated in crude form by dilution with a large volume of water followed by filtration or by extraction into an appropriate organic solvent such as diethyl ether, ethyl acetate, or a halogenated hydrocarbon solvent such as chloroform or methylene chloride. The product can be further purified by chromatography on silica gel, crystallization or prolonged stirring in an appropriate solvent followed by filtration.

The ester product of formula VI thus obtained can be hydrolyzed to the corresponding carboxylic acid derivative under basic conditions, using an aqueous solution of an alkali base such as an alkali carbonate or preferably sodium or potassium hydroxide, with an organic cosolvent such as tetrahydrofuran or a primary, secondary or tertiary alkanol, such as methanol or ethanol, or a combination thereof at temperatures ranging from room temperature to reflux temperature for the appropriate time. The resultant carboxylic acid is isolated in crude form following acidification using an aqueous solution of an inorganic acid such as hydrochloric, sulfuric or a similar acid, and filtration or extraction into an appropriate organic solvent such as diethyl ether, ethyl acetate, or a halogenated hydrocarbon solvent such as chloroform or methylene chloride. The product can be further purified by chromatography on silica gel, crystallization or prolonged stirring in an appropriate solvent followed by filtration. The carboxylic acid is then transformed into the appropriate primary, secondary or tertiary amide analog of formula VII by any general procedure well known to the organic chemist, preferably via initial transformation into a mixed anhydride by treatment with a small excess, usually 1.25 equivalents, of an appropriate alkyl chloroformate such as ethyl or isobutyl chloroformate, in the presence of a larger excess, usually 2.5 equivalents, of a tertiary organic amine such as triethylamine or N,N-diisopropylethylamine in an organic solvent such as tetrahydrofuran at low temperature, preferably 0° C. for a period of 30 minutes to 3 hours. Alternatively, the acid may be transformed into an acid chloride through the action of, for instance, thionyl chloride. An excess, usually 5 or more equivalents, of an appropriate primary or secondary amine or of an aqueous solution of ammonium hydroxide is then added and the reaction is allowed to proceed at a temperature ranging from 0° C. to room temperature for an appropriate length of time, usually 1–24 hours. The desired amide of formula VII is then isolated in crude form by precipitation with water and filtration or extraction into an appropriate organic solvent such as diethyl ether, ethyl acetate, or a halogenated hydrocarbon solvent such as chloroform or methylene chloride. The product can be further purified by chromatography on silica gel, crystallization or prolonged stirring in an appropriate solvent followed by filtration. Alternatively, an amide of formula VII can be obtained from an acid and an amine via an appropriate coupling reagent, such as carbonyldiimidazole (CDI). In cases where the amide moiety is 2,6-dichloropyridin-4-yl a different procedure is used in which the anion of 4-amino-3,5-dichloropyridine is generated at low temperature, preferably at 0° C. using a strong alkali hydride such as sodium hydride in a solvent such as tetrahydrofuran, and reacted with the acid chloride of a carboxylic acid (from hydrolysis of an ester of formula VI) generated by an appropriate known procedure, usually by the action of oxalyl chloride activated by a catalytic amount of N,N-dimethylformamide in a solvent such as tetrahydrofuran.

For the synthesis of compounds of formula I, an amide compound of formula VII is reacted with an appropriately substituted acetylene of formula VIII under the catalysis of a transition metal species such as bis(triphenylphosphine)palladium (II) chloride or [1,1'-bis(diphenylphosphino)ferrocene]dichloropalladium(II) in an appropriate solvent such as THF or DMF in the presence of triethylamine and a cuprous salt such as cuprous iodide, at a temperature ranging from room temperature to reflux for an appropriate period of time. Alternatively, an ester compound of formula VI can be reacted in the same manner to afford an ester compound of formula IX, which is submitted to the hydrolysis and amidation processes described above leading to a compound of formula I.

Scheme 1

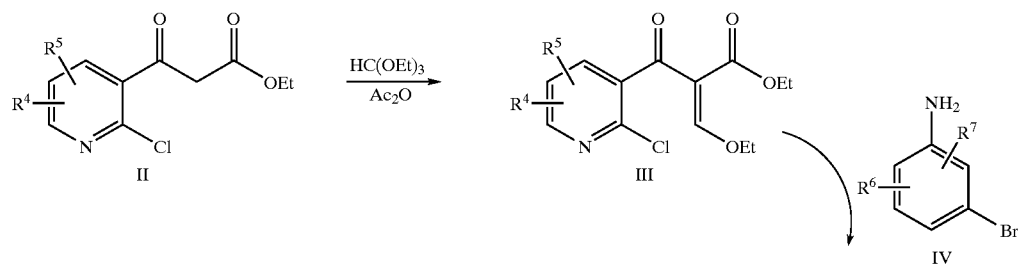

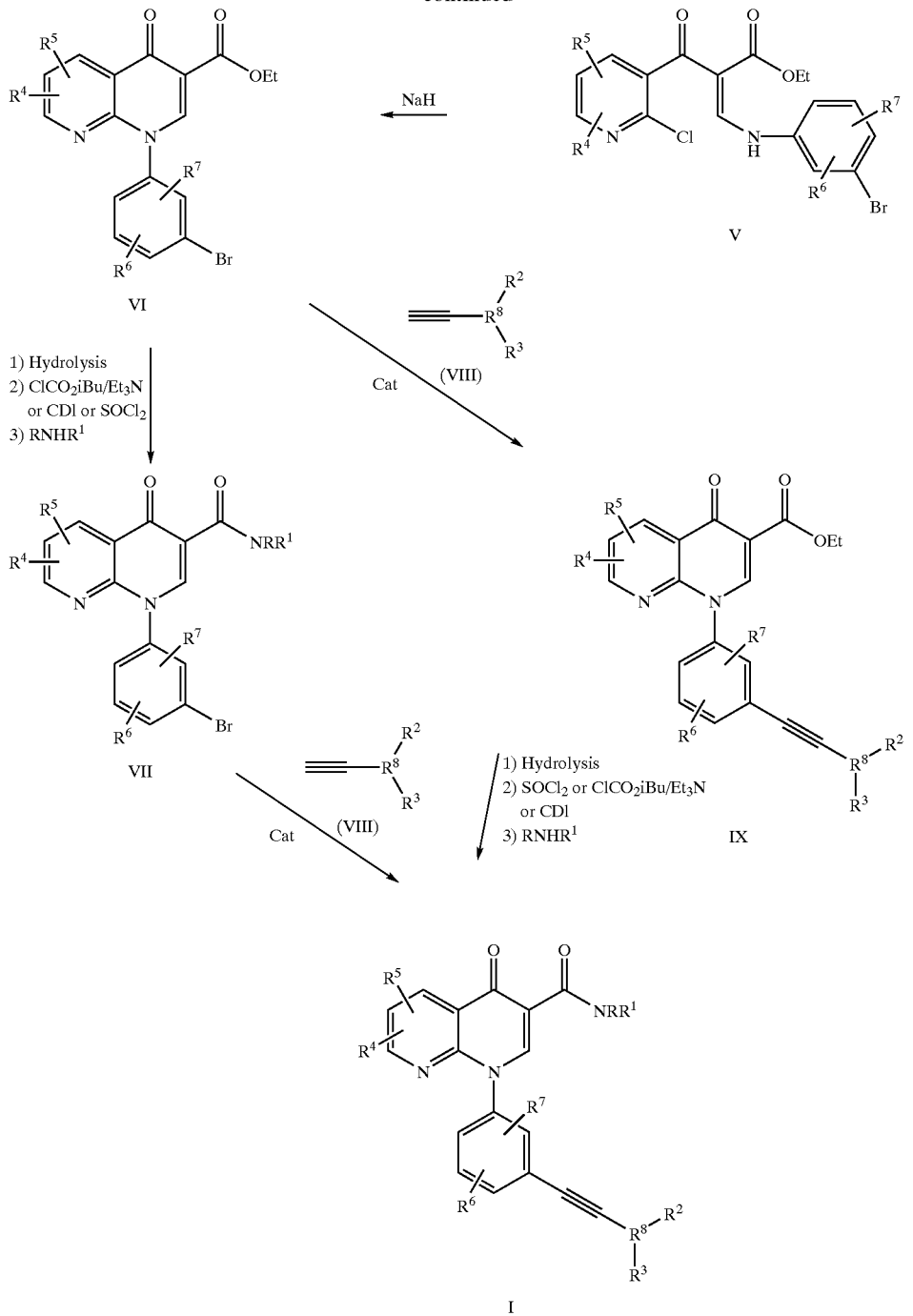

In a second approach to the synthesis of compounds of formula I, outlined below in Scheme 2, an amide of formula VII is reacted with trimethylsilylacetylene under the catalysis of a transition metal species such as bis(triphenylphosphine)palladium (II) chloride or [1,1'-bis(diphenylphosphino)ferrocene]dichloropalladium(II) in an appropriate solvent such as THF or DMF in the presence of triethylamine and a cuprous salt such as cuprous iodide, at a temperature ranging from room temperature to reflux for an appropriate period of time. The resulting compound is liberated from the TMS protecting group under the action of an aqueous solution of an alkali hydroxide such as sodium or potassium hydroxide in the presence of an organic cosolvent such as methanol, or alternatively by treatment with a source of fluoride such as tetrabutylammonium fluoride in THF solution to yield an acetylene derivative of formula X.

Such a compound is reacted with an appropriate alkyl or aryl or heteroaryl halide of formula XI under the catalysis of a transition metal species such as bis(triphenylphosphine)palladium (II) chloride or [1,1'-bis(diphenylphosphino)ferrocene]dichloropalladium(II) in an appropriate solvent such as THF or DMF in the presence of triethylamine and a cuprous salt such as cuprous iodide, at a temperature ranging from room temperature to reflux for an appropriate period of time, to yield a compound of formula I. Alternatively, an ester compound of formula VI can be processed in the same manner to afford an ester compound of formula IX, which is submitted to the hydrolysis and amidation processes described above leading to a compound of formula I.

ethyl 3-dimethylaminoacrylate, in the presence of a tertiary amine such as triethylamine, in a solvent such as toluene at an appropriate temperature to afford a 3-dialkylamino acrylate of formula XIV. Such a substance is reacted with an appropriately substituted 3-aminophenylacetylene deriva-

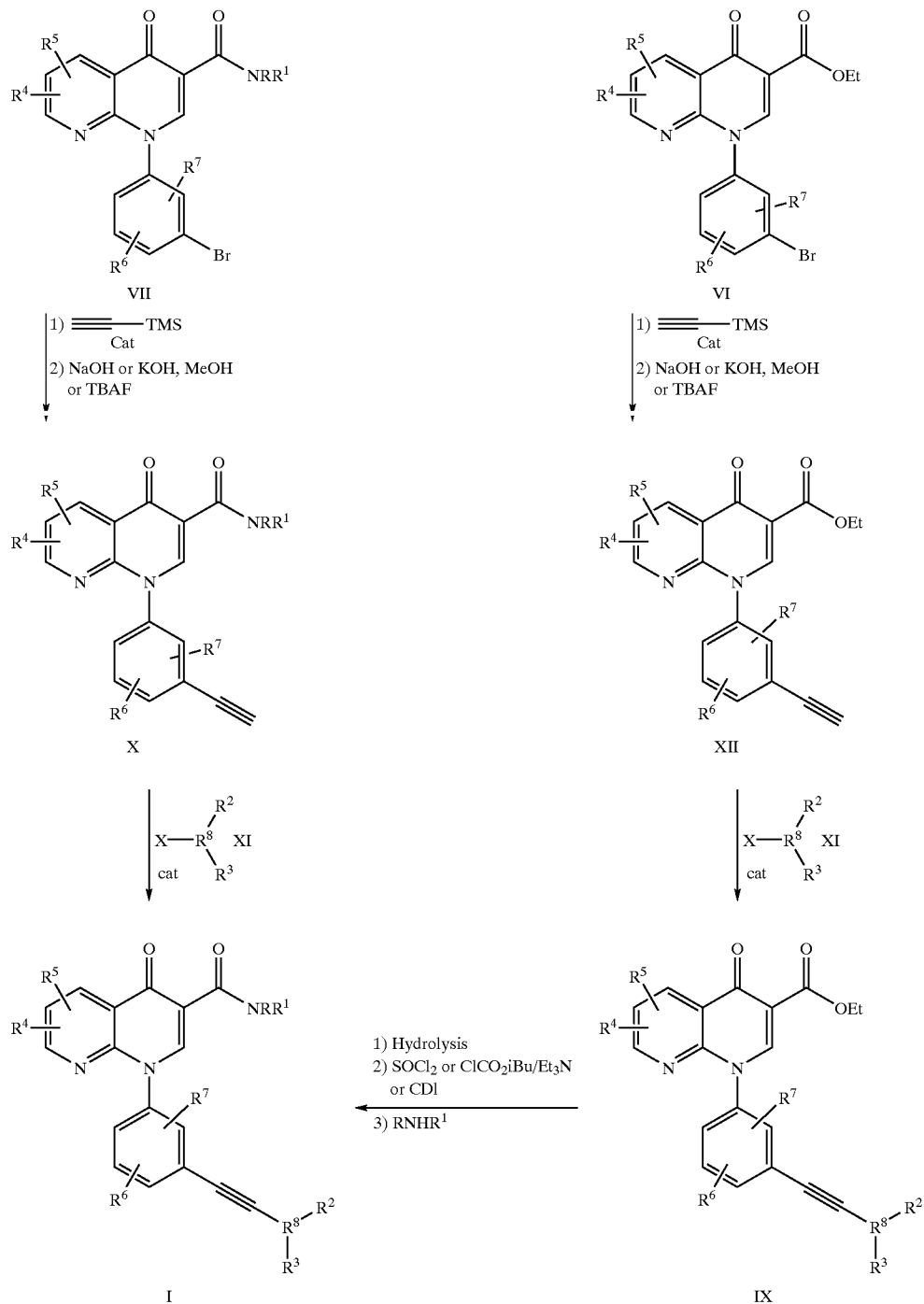

Scheme 2

In an alternative approach to acetylenic esters of formula IX or XII (where $R^8$=H), outlined in Scheme 3, an appropriately substituted 2-chloronicotinoyl chloride of formula XIII is reacted with a 3-dialkylaminoacrylate, for example tive of formula XV in a solvent such as DMF or acetonitrile in the presence of an inorganic base such as potassium carbonate at an appropriate temperature to yield an acetylenic ester of formula IX or XII (where $R^8$=H).

Scheme 3

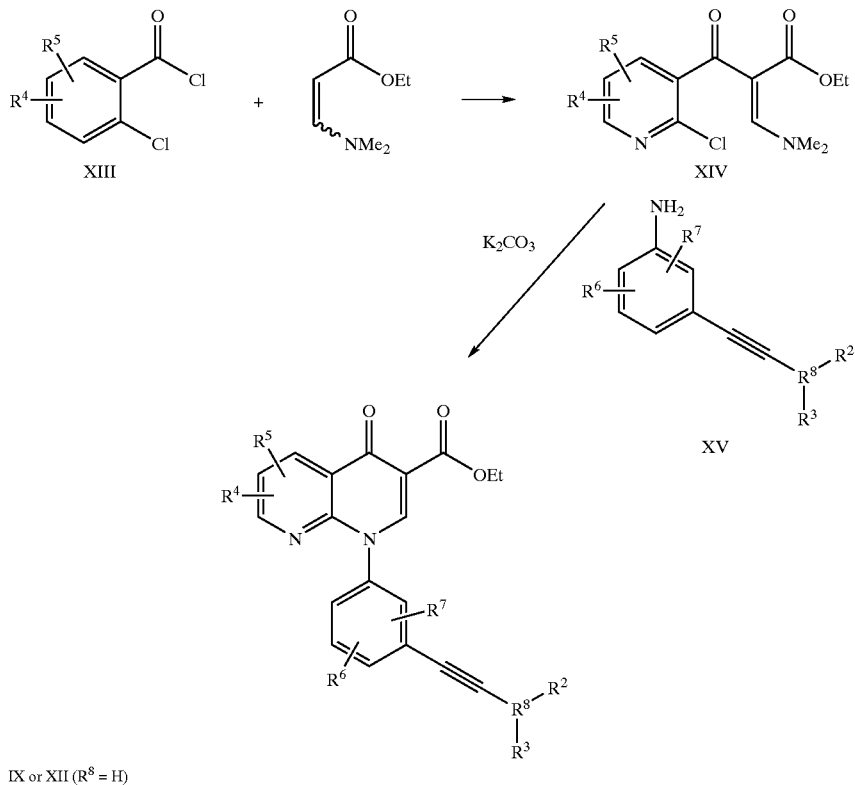

IX or XII (R⁸ = H)

The majority of the acetylenic reagents of formula VIII used in this invention were of commercial sources. Where required, appropriately substituted acetylenes of formula VIII were synthesized as outlined in Scheme 4, preferentially from corresponding halides (XI) by initial condensation with trimethylsilylacetylene under the catalysis of a transition metal species, followed by removal of the TMS group, as described above in Scheme 2 in the preparation of compounds of type X or XII. Where the substituent $R^8$ on the acetylene is a secondary or tertiary alcohol, the anion of trimethylsilylacetylene is generated at low temperature, using a an alkyllithium base such as n-butyllithium, and it can be reacted with an appropriately substituted aldehyde or ketone to afford the desired reagent of formula VIII.

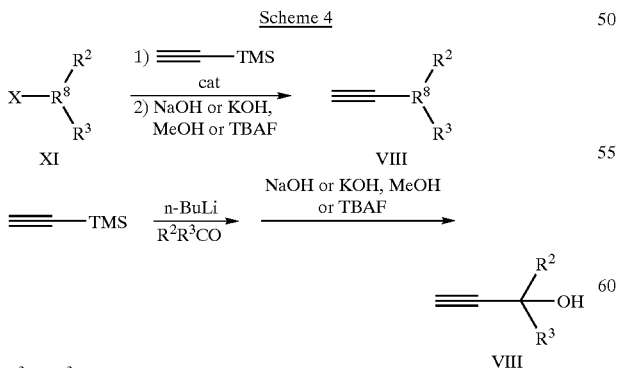

$R^2$ and $R^3$ can be the same or different; $R^3$ can be H

The following are examples of syntheses of aryl and heteroaryl halides corresponding to compounds of formula XI bearing a secondary or tertiary alcohol as substituent. For pyridine derivatives (Scheme 5), a halogen-substituted pyridyl carboxylate of formula XVI can be reacted with an organometallic species such as a Grignard reagent to afford a tertiary alcohol of formula XVII. Alternatively, a dibromopyridine substrate of formula XVIII may be monometallated using an alkyllithium species such as n-butyllithium, followed by addition of an aldehyde or ketone to yield a compound of formula XVII.

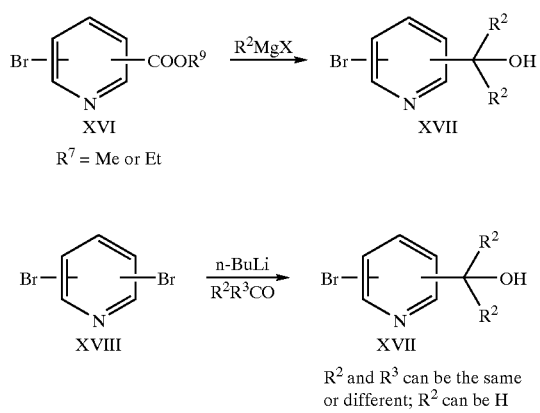

$R^2$ and $R^3$ can be the same or different; $R^2$ can be H

A thiophene derivative of formula XX results from the reaction of a halogen substituted thiophene aldehyde or ketone of formula XIX (Scheme 6) with an organometallic species such as a Grignard reagent.

Scheme 6

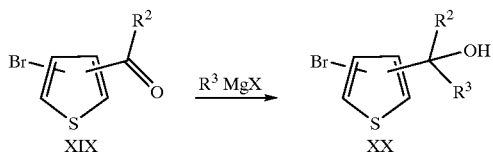

R² and R³ can be the same or different; R² can be H

For the synthesis of the thiazole derivatives of formula XXII, described in Scheme 7, initial metallation of thiazole using an alkyllithium species such as n-butyllithium, followed by addition of an aldehyde or ketone yields a 2-thiazolyl secondary or tertiary alcohol which is suitably protected, for example as a SEM ether of formula XXI. Subsequent bromination leads to introduction of a bromo atom at the 5-position with concomitant removal of the protective group, resulting in a compound of formula XXII.

Scheme 7

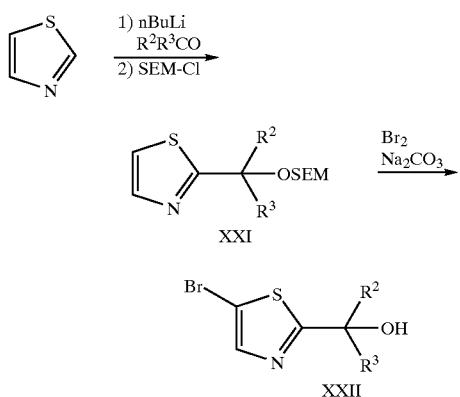

R² and R³ can be the same or different; R³ can be H

Where required, pyridine derivatives can be oxidized to the corresponding N-oxides using well-known reagents such as m-chloroperoxybenzoic acid or magnesium monoperoxyphthalate.

EXAMPLES

Referring to the formula below, Examples 1–33 are summarized in TABLE 1 below.

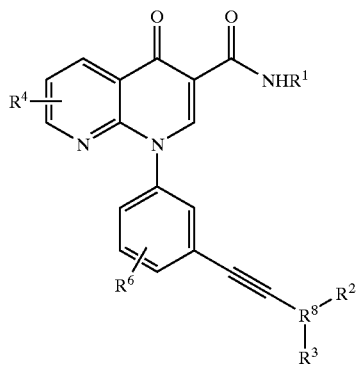

TABLE 1

| Ex. | R¹ | R⁸R²R³ | R⁴ | R⁶ |
|---|---|---|---|---|
| 1 | i-pr | Ph | H | H |
| 2 | i-pr | 2-Pyr | H | H |
| 3 | i-pr | 4-Pyr | H | H |
| 4 | i-pr | 4-Pyr NO | H | H |
| 5 | i-pr | H | H | H |
| 6 | c-pr | H | H | H |
| 7 | i-pr | 3-Pyr | H | H |
| 8 | i-pr | 3-Pyr NO | H | H |
| 9 | c-pr | 3-Pyr | H | H |
| 10 | i-pr | –C(Me)(Me)OH | H | H |
| 11 | c-pr | –C(Me)(Me)OH | H | H |
| 12 | i-pr | 1-hydroxycyclopentyl | H | H |
| 13 | i-pr | 1-hydroxycyclopropyl | H | H |
| 14 | i-pr | –C(CF₃)(CF₃)OH | H | H |
| 15 | i-pr | –C(Me)(Ph)OH | H | H |
| 16 | c-pr | 3-Pyr NO | H | H |
| 17 | i-pr | –C(Et)(Et)NH₂ | H | H |
| 18 | c-pr | –C(Et)(Et)NH₂ | H | H |
| 19 | i-pr | 3-quinolinyl | H | H |
| 20 | i-pr | 3-quinolinyl N-oxide | H | H |
| 21 | i-pr | cyclopropyl | H | H |

TABLE 1-continued
| Ex. | R¹ | R⁸R²R³ | R⁴ | R⁶ |
|---|---|---|---|---|
| 22 | i-pr | 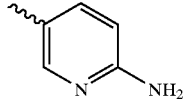 | H | H |
| 23 | i-pr | 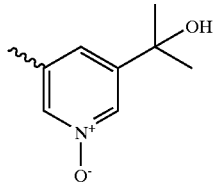 | H | H |
| 24 | i-pr | 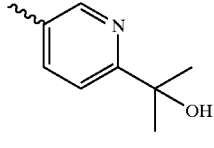 | H | H |
| 25 | i-pr | 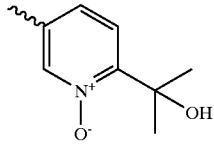 | H | H |
| 26 | i-pr | 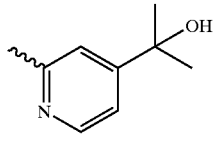 | H | H |
| 27 | i-pr | 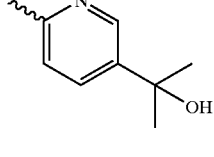 | H | H |
| 28 | i-pr | 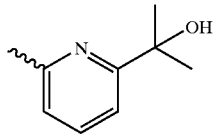 | H | H |
TABLE 1-continued
| Ex. | R¹ | R⁸R²R³ | R⁴ | R⁶ |
|---|---|---|---|---|
| 29 | c-pr | 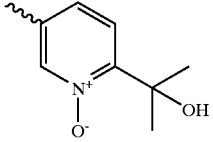 | H | H |
| 30 | i-pr | 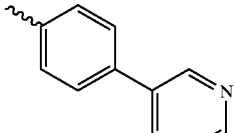 | H | H |
| 31 | i-pr | 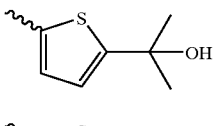 | H | H |
| 32 | i-pr | 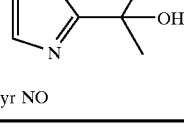 | H | H |
| 33 | H | 3-Pyr NO | H | H |
Referring to the formula below, Examples 35–53 are summarized in TABLE 2 below.
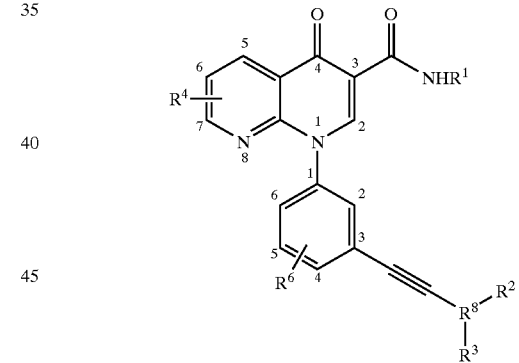
TABLE 2
| Ex. | R¹ | R⁸R²R³ | R⁴ | R⁶ |
|---|---|---|---|---|
| 35 | 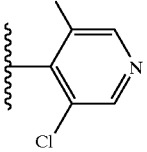 | 3-Pyr-NO | H | H |
| 36 | c-Bu | 3-(OH)Ph | 6-Me | H |
| 37 | 3-Pyr | Ph | H | 5-Me |

TABLE 2-continued
| Ex. | R¹ | R⁸R²R³ | R⁴ | R⁶ |
|---|---|---|---|---|
| 38 | CH₂Ph | 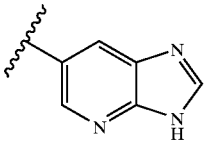 | H | H |
| 39 | 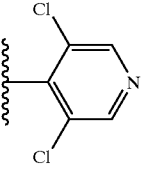 | 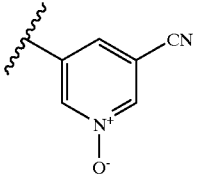 | H | H |
| 40 |  | 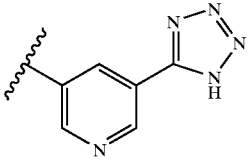 | 7-Me | H |
| 41 | Ph | 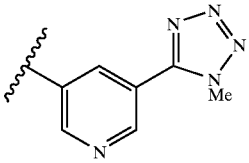 | 6-Cl | H |
| 42 | 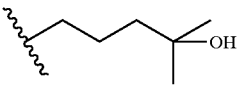 | 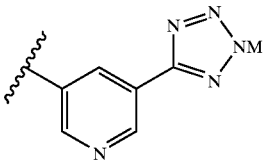 | H | 4-Cl |
| 43 | 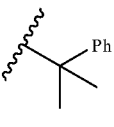 | 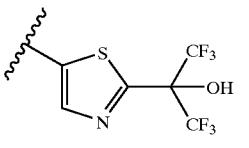 | H | H |
| 44 | 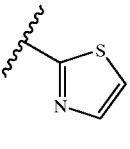 | 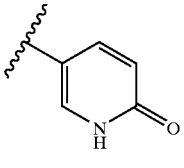 | H | 5-OH |
| 45 | 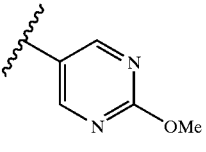 | 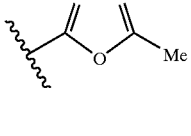 | H | H |
| 46 |  | 3-Pyr-NO | H | H |

TABLE 2-continued

| Ex. | R¹ | R⁸R²R³ | R⁴ | R⁶ |
|---|---|---|---|---|
| 47 | cyclopropyl-OH (cis & trans) | 3-Pyr-NO | H | H |
| 48 | -O-propyl | 5-indolyl (1H) | H | H |
| 49 | SO₂Ph | 2-ethyl-1,3,4-thiadiazol-5-yl | H | H |
| 50 | -CH₂CH₂N(Me)₂ | 5-(2-hydroxyprop-2-yl)pyridin-3-yl | H | 5-F |
| 51 | -C(O)-cyclohexyl | 3-methyl-1,2,4-oxadiazol-5-yl | 5-OH | H |
| 52 | Me | 1,2,5-thiadiazol-3-yl | H | H |
| 53 | Et | quinoline-6-yl N-oxide | H | H |

Example 1

N-Isopropyl-1-[3-(phenylethynyl)phenyl]-1,4-dihydro[1,8]naphthyridin-4-one-3-carboxamide Step 1: Ethyl 3-(3-bromoanilino)-2-(2-chloronicotinoyl)acrylate.

A mixture of ethyl 2-chloronicotinoyl acetate (41.1 g, 180.5 mmol), triethyl orthoformate (40.12 g, 271 mmol) and acetic anhydride (92.05 g, 902.5 mmol) was heated at 130° C. for 2.5 hours. The volatile components were distilled off and the resulting residue was co-evaporated twice with xylene. The oily residue was dissolved in methylene chloride (250 mL) and 3-bromoaniline (37.25 g, 216.6 mmol) was added slowly. The resulting solution was stirred at room temperature for 18 hours, and the solvent evaporated away. The resulting crude compound was used as such in the next step.

Step 2: Ethyl 1-(3-bromophenyl)-1,4-dihydro[1,8]naphthyridin-4-one-3-carboxylate.

The crude compound from Step 1 was dissolved in tetrahydrofuran (500 mL), the solution was cooled to 0° C., and sodium hydride (as a 60% dispersion in oil, 9.4 g, 235 mmol) was added in portions. After stirring at 0° for 1 hour, the resulting mixture was allowed to warm up to room temperature. After 2 hours, water (400 mL) was added to the resulting suspension and the insoluble solid was filtered and washed copiously with water. When dry, the solid was stirred in ether (150 ML) at room temperature for 24 hours and filtered to afford the ethyl 1-(3-bromophenyl)-1,4-dihydro[1,8]naphthyridin-4-one-3-carboxylate compound as a cream-colored solid.

$^1$H NMR (Acetone-$d_6$) δ 1.32 (t, 3H), 4.29 (q, 2H), 7.54–7.63 (m, 2H), 7.69 (dd, 1H), 7.78 (dd, 1H), 7.93 (s, 1H), 8.66–8.71 (m, 3H).

Step 3: 1-(3-Bromophenyl)-1,4-dihydro[1,8]naphthyridin-4-one-3-carboxylic Acid.

A suspension of ethyl 1-(3-bromophenyl)-1,4-dihydro[1,8]naphthyridin-4-one-3-carboxylate from Step 2 (52.5 g, 140.7 mmol) in a mixture of tetrahydrofuran (400 mL), methanol (400 mL) and 1N aqueous sodium hydroxide (280 mL) was heated at ca 50° C. with stirring for 20 minutes.

After cooling, the mixture was diluted with water (300 mL) and 1N aqueous HCl (325 mL) was added. After stirring for 45 minutes, the precipitate was filtered, washed well with water and dried to afford the 1-(3-bromophenyl)-1,4-dihydro[1,8]naphthyridin-4-one-3-carboxylic acid as a cream-colored solid.

$^1$H NMR (Acetone-$d_6$) δ 7.65 (t, 1H), 7.76 (m, 2H), 7.84 (d, 1H), 7.99 (s, 1H), 8.87 (m, 2H), 9.01 (s, 1H).

Step 4: N-Isopropyl-1-(3-bromophenyl)-1,4-dihydro[1,8]naphthyridin-4-one-3-carboxamide.

To a suspension of 1-(3-bromophenyl)-1,4-dihydro[1,8]naphthyridin-4-one-3-carboxylic acid from Step 3 (26.3 g, 76 mmol) and triethylamine (23.2 g, 230 mmol) in tetrahydrofuran (1000 mL) at 0° C. was added isobutyl chloroformate (18.85 g, 138 mmol). After stirring at 0° C. for 2 hours, isopropylamine (23 g, 390 mmol) was added and the mixture was allowed to warm up to room temperature and stirred overnight. The mixture was then partitioned between ethyl acetate and water, the organic phase was dried and evaporated to a solid which was stirred in ether at room temperature for 3 hours and filtered to afford the N-isopropyl-1-(3-bromophenyl)-1,4-dihydro[1,8]naphthyridin-4-one-3-carboxamide as a white solid.

$^1$H NMR (Acetone-$d_6$) δ 1.25 (d, 6H), 4.17 (m, 1H), 7.59–7.63 (m, 2H), 7.70 (d, 1H), 7.80 (d, 1H), 7.94 (s, 1H), 8.73 (m, 1H), 8.78 (d, 1H), 8.85 (s, 1H), 9.61 (br, NH).

Step 5: N-Isopropyl-1-[(3-phenylethynyl)phenyl]-1,4-dihydro[1,8]naphthyridin-4-one-3-carboxamide.

A mixture of amide from Step 4, phenylacetylene (1.9 eq), triethylamine (1.6 eq), triphenylphosphine (0.06 eq) and bis(triphenylphosphine)palladium(II) chloride (0.05 eq) in THF (16 mL/mmol) was stirred at room temperature for 20 minutes. Copper(I) iodide (5 mg/mmol) was added and the mixture was stirred at reflux for 18 hours. After cooling, the mixture was quenched with saturated aqueous ammonium chloride solution and partitioned between ethyl acetate and water. The organic phase was dried over magnesium sulfate and the crude product was chromatographed on silica gel eluting with a 1:9 mixture of ether and methylene chloride to afford a solid which was stirred in ether at room temperature and filtered to yield the N-Isopropyl-1-[(3-phenylethynyl)phenyl]-1,4-dihydro[1,8]naphthyridin-4-one-3-carboxamide compound as a solid.

$^1$H NMR (Acetone-$d_6$) δ 1.24 (d, 6H), 4.18 (m, 1H), 7.42 (m, 3H), 7.56–7.61 (m, 3H), 7.69 (m, 2H), 7.76 (m, 1H), 7.85 (s, 1H), 8.73 (m, 1H), 8.77 (dd, 1H), 8.88 (s, 1H), 9.62 (br, NH).

Example 2

N-Isopropyl-1-[3-(2-pyridinylethynyl)phenyl]-1,4-dihydro[1,8]naphthyridin-4-one-3-carboxamide Following the procedure of Step 5 of EXAMPLE 1, but substituting 2-ethynylpyridine for phenylacetylene, the title compound was obtained as a brown solid.

$^1$H NMR (Acetone-$d_6$) δ 1.25 (d, 6H), 4.18 (m, 1H), 7.38 (m, 1H), 7.59–7.64 (m, 2H), 7.71–7.76 (m, 2H), 7.81–7.85 (m, 2H), 7.92 (s, 1H), 8.61 (m, 1H), 8.74 (m, 1H), 8.78 (dd, 1H), 8.89 (s, 1H), 9.62 (br, NH).

Example 3

N-Isopropyl-1-[3-(4-pyridinylethynyl)phenyl]-1,4-dihydro[1,8]naphthyridin-4-one-3-carboxamide Following the procedure of Step 5 of EXAMPLE 1, but substituting 4-ethynylpyridine (*J.Org.Chem.* 1996, 61, 6535) for phenylacetylene, the title compound was obtained as a solid.

$^1$H NMR (Acetone-$d_6$) δ 1.24 (d, 6H), 4.18 (m, 1H), 7.49 (m, 2H), 7.61 (m, 1H), 7.71–7.78 (m, 2H), 7.81 (m, 1H), 7.92 (s, 1H), 8.62 (m, 2H), 8.73 (m, 8.78 (dd, 1H), 8.87 (s, 1H), 9.62 (br, NH).

Example 4

N-Isopropyl-1-[3-(1-oxido-4-pyridinylethynyl)phenyl]-1,4-dihydro[1,8]naphthyridin-4-one-3-carboxamide To a solution of N-Isopropyl-1-[3-(4-pyridinylethynyl)phenyl]-1,4-dihydro[1,8]naphthyridin-4-one-3-carboxamide from EXAMPLE 3 in methylene chloride (36 mL/mmol) and methanol (3 mL/mmol) was added magnesium monoperoxyphthalate hexahydrate (MMPP, 3.6 eq) and the mixture was stirred at room temperature overnight. A further amount of MMPP (2 eq) was added and stirring was continued for 24 hours. The resulting mixture was filtered through a bed of celite, the filtrate was diluted with methylene chloride and washed with aqueous sodium bicarbonate and water. After drying, the organic phase was evaporated and the crude product was purified by chromatography on silica gel eluting with 10% methanol in methylene chloride to afford the title compound as a solid.

$^1$H NMR (CDCl$_3$) δ 1.28 (d, 6H), 4.28 (m, 1H), 7.35 (d, 2H), 7.46 (m, 2H), 7.58 (m, 2H), 7.67 (m, 1H), 8.14 (d, 2H), 8.69 (m, 1H), 8.81 (dd, 1H), 8.99 (s, 1H), 9.62 (br, NH).

Example 5

N-Isopropyl-1-(3-ethynylphenyl)-1,4-dihydro[1,8]naphthyridin-4-one-3-carboxamide Step 1: N-Isopropyl-1-[3-(trimethylsilylethynyl)phenyl]-1,4-dihydro[1,81]naphthyridin-4-one-3-carboxamide.

Following the procedure of Step 5 of EXAMPLE 1, but substituting trimethylsilylacetylene for phenylacetylene, the N-isopropyl-1-[3-(trimethylsilylethynyl)phenyl]-1,4-dihydro[1,8]naphthyridin-4-one-3-carboxamide product was obtained and used in the next step without further purification.

Step 2: N-Isopropyl-1-(3-ethynylphenyl)-1,4-dihydro[1,8]naphthyridin-4-one-3-carboxamide.

The crude product from Step 1 was dissolved in methanol (12 mL/mmol) and 1N aqueous sodium hydroxide was added (3 eq), resulting in a suspension. The suspension mixture was stirred at room temperature for 2 hours and the methanol was evaporated. The resulting aqueous suspension was diluted with water and the product was extracted out with ethyl acetate. The crude product was chromatographed on silica gel eluting with 10% ether in methylene chloride to afford the N-isopropyl-1-(3-ethynylphenyl)-1,4-dihydro[1,8]naphthyridin-4-one-3-carboxamide compound as a solid.

$^1$H NMR (Acetone-$d_6$) δ 1.24 (d, 6H), 3.81 (s, 1H), 4.17 (m, 1H), 7.59 (m, 1H), 7.64–7.71 (m, 3H), 7.81 (s, 1H), 8.72 (m, 1H), 8.76 (dd, 1H), 8.84 (s, 1H), 9.61 (br, NH).

Example 6

N-Cyclopropyl-1-(3-ethynylphenyl)-1,4-dihydro[1,8]naphthyridin-4-one-3-carboxamide Step 1: N-Cyclopropyl-1-(3-bromophenyl)-1,4-dihydro[1,8]naphthyridin-4-one-3-carboxamide.

Following the procedure of Step 4 of EXAMPLE 1, but substituting cyclopropylamine for isopropylamine, the N-cyclopropyl-1-(3-bromophenyl)-1,4-dihydro[1,8]naphthyridin-4-one-3-carboxamide was obtained as a fluffy white solid.

¹H NMR (Acetone-d₆) δ 0.59 (m, 2H), 0.80 (m, 2h), 2.96 (m, 1H), 7.59–7.68 (m, 2H), 7.72 (dd, 1H), 7.82 (dd, 1H), 7.97 (s, 1H), 8.72–8.81 (m, 2H), 8.89 (s, 1H), 9.70 (br, NH).
Steps 2 and 3: N-Cyclopropyl-1-(3-ethynylphenyl)-1,4-dihydro[1,8]naphthyridin-4-one-3-carboxamide Following the procedures of Steps 1 and 2 of EXAMPLE 5, but substituting the product from step 1 for N-isopropyl-1-(3-bromophenyl)-1,4-dihydro[1,8]naphthyridin-4-one-3-carboxamide, the N-Cyclopropyl-1-(3-ethynylphenyl)-1,4-dihydro[1,8]naphthyridin-4-one-3-carboxamide compound was obtained as a solid.

¹H NMR (CDCl₃) δ 0.66 (m, 2H), 0.85 (m, 2H), 2.97 (m, 1H), 3.18 (s, 1H), 7.42 (d, 1H), 7.47 (m, 1H), 7.52–7.58 (m, 2H), 7.65 (d, 1H), 8.70 (m, 1H), 8.80 (dd, 1H), 8.98 (s, 1H), 9.74 (br, NH).

Example 7

N-Isopropyl-1-[3-(3-pyridinylethynyl)phenyl]-1,4-dihydro[1,8]naphthyridin-4-one-3-carboxamide Following the procedure of Step 5 of EXAMPLE 1, but substituting N-isopropyl-1-(3-ethynylphenyl)-1,4-dihydro[1,8]naphthyridin-4-one-3-carboxamide from EXAMPLE 5 for phenylacetylene and 3-bromopyridine for N-isopropyl-1-(3-bromophenyl)-1,4-dihydro[1,8]naphthyridin-4-one-3-carboxamide, the title compound was obtained as a light brown solid.

¹H NMR (Acetone-d₆) δ 1.24 (d, 6H), 4.18 (m, 1H), 7.43 (m, 1H), 7.61 (m, 1H), 7.70–7.75 (m, 2H), 7.80 (d, 1H), 7.90 (s, 1H), 7.94 (d, 1H), 8.58 (m, 1H), 8.74–8.79 (m, 3H), 8.88 (s, 1H), 9.62 (br, NH).

Example 8

N-Isopropyl-1-[3-(1-oxido-3-pyridinylethynyl)phenyl]-1,4-dihydro[1,8]naphthyridin-4-one-3-carboxamide Following the procedure of EXAMPLE 4, but substituting N-isopropyl-1-[3-(3-pyridinylethynyl)phenyl]-1,4-dihydro[1,8]naphthyridin-4-one-3-carboxamide from EXAMPLE 7 for N-isopropyl-1-[3-(4-pyridinylethynyl)phenyl]-1,4-dihydro[1,8]naphthyridin-4-one-3-carboxamide, the title compound was obtained as a solid.

¹H NMR (CDCl₃) δ 1.28 (d, 6H), 4.28 (m, 1H), 7.26 (m, 1H), 7.36 (d, 1H), 7.45–7.49 (m, 2H), 7.57–7.62 (m, 2H), 7.69 (d, 1H), 8.16 (d, 1H), 8.31 (s, 1H), 8.69 (m, 1H), 8.81 (dd, 1H), 8.99 (s, 1H), 9.63 (br, NH).

Example 9

N-Cyclopropyl-1-[3-(3-pyridinylethynyl)phenyl]-1,4-dihydro[1,8]naphthyridin-4-one-3-carboxamide Following the procedure of Step 5 of EXAMPLE 1, but substituting N-cyclopropyl-1-(3-ethynylphenyl)-1,4-dihydro[1,8]naphthyridin-4-one-3-carboxamide from EXAMPLE 6 for phenylacetylene and 3-bromopyridine for N-isopropyl-1-(3-bromophenyl)-1,4-dihydro[1,8]naphthyridin4-one-3-carboxamide, the title compound was obtained as a solid.

¹H NMR (CDCl₃) δ 0.66 (m, 2H), 0.85 (m, 2H), 2.97 (m, 1H), 7.28 (m, 1H), 7.43–7.48 (m, 2H), 7.57 (t, 1H), 7.62 (s, 1H), 7.70 (d, 1H), 7.79 (d, 1H), 8.55 (m, 1H), 8.70 (m, 1H), 8.75 (s, 1H), 8.79 (dd, 1H), 9.01 (s, 1H), 9.74 (br, NH).

Example 10

N-Isopropyl-1-[3-(3-hydroxy-3-methylbut-1-ynyl)phenyl]-1,4-dihydro[1,8]naphthyridin-4-one-3-carboxamide Following the procedure of Step 5 of EXAMPLE 1, but substituting 2-methyl-3-butyn-2-ol for phenylacetylene, the title compound was obtained as a white solid.

¹H NMR (Acetone-d₆) δ 1.24 (d, 6H), 1.53 (s, 6H), 4.17 (m, 1H), 4.52 (s, 1H, OH), 7.58–7.65 (m, 4H), 7.68 (s, 1H), 8.72 (m, 1H), 8.77 (dd, 1H), 8.84 (s, 1H), 9.62 (br, NH).

Example 11

N-Cyclopropyl-1-[3-(3-hydroxy-3-methylbut-1-ynyl)phenyl]-1,4-dihydro[1,8]naphthyridin-4-one-3-carboxamide Following the procedure of EXAMPLE 10, but substituting N-cyclopropyl-1-(3-ethynylphenyl)-1,4-dihydro[1,8]naphthyridin-4-one-3-carboxamide from EXAMPLE 6 for N-isopropyl-1-(3-ethynylphenyl)-1,4-dihydro[1,8]naphthyridin-4-one-3-carboxamide, the title compound was obtained as a white solid.

¹H NMR (Acetone-d₆) δ 0.57 (m, 2H), 0.78 (m, 2H), 1.53 (s, 6H), 2.93 (m, 1H), 4.53 (s, 1H, OH), 7.58–7.65 (m, 4H), 7.67 (s, 1H), 8.72 (m, 1H), 8.76 (dd, 1H), 8.85 (s, 1H), 9.69 (br, NH).

Example 12

N-Isopropyl-1-[3-(1-hydroxycyclopentyl)ethynylphenyl]-1,4-dihydro[1,8]naphthyridin-4-one-3-carboxamide Following the procedure of Step 5 of EXAMPLE 1, but substituting 1-ethynylcyclopentanol for phenylacetylene, the title compound was obtained as a white solid.

¹H NMR (CDCl₃) δ 1.28 (d, 6H), 1.76–1.80 (m, 2H), 1.84–1.88 (m, 3H), 1.98–2.06 (m, 4H), 4.27 (m, 1H), 7.36 (d, 1H), 7.44–7.50 (m, 3H), 7.5 (d, 1H), 8.68 (m, 1H), 8.79 (dd, 1H), 8.97 (s, 1H), 9.63 (br, NH).

Example 13

N-Isopropyl-1-[3-(1-hydroxycyclopropyl)ethynylphenyl]-1,4-dihydro[1,8]naphthyridin-4-one-3-carboxamide Step 1: 1-Ethynylcyclopropanol.

The 1-ethynylcyclopropanol was prepared following the procedure described in *J. Org. Chem.* 1976, 41, 1237 from [(1-ethoxycyclopropyl)oxy]trimethylsilane and ethynyl magnesium bromide and was obtained as a liquid.

Step 2: N-Isopropyl-1-[3-(1-hydroxycyclopropyl)ethynylphenyl]-1,4-dihydro[1,8]naphthyridin-4-one-3-carboxamide.

Following the procedure of Step 5 of EXAMPLE 1, but substituting the product from present Step 1 for phenylacetylene, the N-isopropyl-1-[3-(1-hydroxycyclopropyl)ethynylphenyl]-1,4-dihydro[1,8]naphthyridin-4-one-3-carboxamide compound was obtained as a solid.

¹H NMR (CDCl₃) δ 1.09 (m, 2H), 1.17 (m, 2H), 1.28 (d, 6H), 2.57 (s, 1H, OH), 4.28 (m, 1H), 7.35 (d, 1H), 7.44–7.50 (m, 3H), 7.54 (d, 1H), 8.68 (m, 1H), 8.79 (dd, 1H), 8.96 (s, 1H), 9.63 (br, NH).

Example 14

N-Isopropyl-1-{3-[4,4,4-trifluoro-3-hydroxy-3-(trifluoromethyl)but-1-ynyl]phenyl}-1,4-dihydro[1,8]naphthyridin-4-one-3-carboxamide Step 1: 1,1,1-Trifluoro-2-(trifluoromethyl)-4-(trimethylsilyl)but-3-yn-2-ol.

To a solution of trimethylsilylacetylene (4 mL) in THF (30 mL) at −78° C. was added 2.5M n-butyllithium in hexanes (14 mL) and the resulting mixture was stirred for 1 hour. An excess of hexafluoroacetone was bubbled into the cold mixture and stirring was continued for 4 hours. After warming to room temperature, the mixture was quenched with saturated aqueous ammonium chloride solution and partitioned between ether and water. The organic phase was dried and evaporated to afford the 1,1,1-trifluoro-2-(trifluoromethyl)-4-(trimethylsilyl)but-3-yn-2-ol as a liquid.
Step 2: N-Isopropyl-1-3-[4,4,4-Trifluoro-3-hydroxy-3-(trifluoromethyl)but-1-ynyl]phenyl-1,4-dihydro[1,8]naphthyridin-4-one-3-carboxamide.

To a solution of 1,1,1-trifluoro-2-(trifluoromethyl)-4-(trimethylsilyl)but-3-yn-2-ol from present Step 1 (6.8 mmol) in 10 mL of THF was added 1M tetrabutylammonium fluoride (8.5 mL) and the resulting mixture was refluxed for 30 minutes to remove the TMS protecting group. The procedure of Step 5 of EXAMPLE 1 was then applied, but substituting this solution for phenylacetylene to afford the N-Isopropyl-1-{3-[4,4,4-trifluoro-3-hydroxy-3-(trifluoromethyl)but-1-ynyl]phenyl}-1,4-dihydro[1,8]naphthyridin-4-one-3-carboxamide compound as a solid.

$^1$H NMR (Acetone-$d_6$) δ 1.24 (d, 6H), 4.17 (m, 1H), 7.60 (m, 1H), 7.72–7.79 (m, 2H), 7.83 (d, 1H), 7.90 (s, 1H), 8.14 (s, 1H, OH), 8.72 (m, 1H), (dd, 1H), 8.85 (s, 1H), 9.62 (br, NH).

Example 15

N-Isopropyl-1-[3-(3-hydroxy-3-phenylbut-1-ynyl) phenyl]-1,4-dihydro [1,8]naphthyridin-4-one-3-carboxamide A mixture of N-isopropyl-1-(3-bromophenyl)-1,4-dihydro[1,8]naphthyridin-4-one-3-carboxamide from Step 4 of EXAMPLE 1, 2-phenyl-3-butyn-2-ol (2 eq), triethylamine (1.66 eq), bis(diphenylphosphino)ferrocene] dichloropalladium(II) (0.05 eq), and copper(I) iodide (5 mg/mmol) in DMF (20 ml/mmol) was heated at 85° C. for 18 hours. After cooling to room temperature, the resulting mixture was quenched with saturated aqueous ammonium chloride solution and partitioned between ethyl acetate and water. The crude product from the organic phase was chromatographed on silica gel eluting with 20% ether in methylene chloride. The purified product was stirred in ether at room temperature for 3 hours and filtered to afford the title compound as a white solid.

$^1$H NMR (Acetone-$d_6$) δ 1.24 (d, 6H), 1.79 (s, 3H), 4.18 (m, 1H), 5.22 (s, 1H, OH), 7.26 (t, 1H), 7.35 (t, 2H), 7.59 (m, 1H), 7.66 (m, 3H), 7.73 (d, 2H), 7.66 (s, 1H), 8.72 (m, 1H), 8.77 (dd, 1H), 8.84 (s, 1H), 9.62 (br, NH).

Example 16

N-Cyclopropyl-1-[3-(1-oxido-3-pyridinylethynyl) phenyl]-1,4-dihydro[1,8]naphthyridin-4-one-3-carboxamide Step 1: 3-Ethynylpyridine N-oxide.

To a solution of 3-ethynylpyridine in methylene chloride (5 mL/mmol) at room temperature was added m-chloroperoxybenzoic acid (m-CPBA, 70% purity, 1.2 eq) and the resulting mixture was stirred for 2 hours. A further amount of m-CPBA was added (0.25 eq) and stirring was continued for 1 hour. Calcium hydroxide was added (2 eq) and after 15 minutes the mixture was filtered through celite and the filtrate was evaporated. The solid residue was stirred in ether for 3 hours and filtered to afford the 3-ethynylpyridine N-oxide compound as a white solid.
Step 2: N-Cyclopropyl-1-[3-(1-oxido-3-pyridinylethynyl) phenyl]-1,4-dihydro[1,8]naphthyridin-4-one-3-carboxamide.

Following the procedure of EXAMPLE 15, but substituting N-cyclopropyl-1-(3-bromophenyl)-1,4-dihydro[1,8] naphthyridin-4-one-3-carboxamide from Step 1 of EXAMPLE 6 for N-isopropyl-1-(3-bromophenyl)-1,4-dihydro[1,8]naphthyridin-4-one-3-carboxamide, and 3-ethynylpyridine N-oxide from Step 1 for 2-phenyl-3-butyn-2-ol, the N-cyclopropyl-1-[3-(1-oxido-3-pyridinylethynyl)phenyl]-1,4-dihydro[1,8]naphthyridin4-one-3-carboxamide compound was obtained as a white solid.

$^1$H NMR (CDCl$_3$) δ 0.66 (m, 2H), 0.84 (m, 2H), 2.96 (m, 1H), 7.26 (m, 1H), 7.37 (d, 1H), 7.45–7.48 (m, 2H), 7.58–7.62 (m, 2H), 7.69 (d, 1H), 8.16 (d, 1H), 8.31 (s, 1H), 8.69 (m, 1H), 8.79 (dd, 1H), 8.99 (s, 1H), 9.73 (br, NH).

Example 17

N-Isopropyl-1-[3-(3-amino-3-ethylpent-1-ynyl) phenyl]-1,4-dihydro[1,8]naphthyridin-4-one-3-carboxamide Following the procedure of EXAMPLE 15, but substituting 1,1-diethylpropargylamine for 2-phenyl-3-butyn-2-ol, the title compound was obtained as a solid.

$^1$H NMR (CDCl$_3$) δ 1.05 (t, 6H), 1.28 (d, 6H), 1.57 (m, 2H), 1.69 (m, 2H), 4.27 (m, 1H), 7.33 (d, 1H), 7.44–7.49 (m, 3H), 7.53 (d, 1H), 8.69 (m, 1H), 8.79 (dd, 1H), 8.97 (s, 1H), 9.63 (br, NH). (NH$_2$ not observed).

Example 18

N-Cyclopropyl-1-[3-(3-amino-3-ethylpent-1-ynyl) phenyl]-1,4-dihydro[1,8]naphthyridin-4-one-3-carboxamide Following the procedure of EXAMPLE 17, but substituting N-cyclopropyl-1-(3-bromophenyl)-1,4-dihydro[1,8] naphthyridin-4-one-3-carboxamide from Step 1 of EXAMPLE 6 for N-isopropyl-1-(3-bromophenyl)-1,4-dihydro[1,8]naphthyridin-4-one-3-carboxamide, the title compound was obtained as a solid.

$^1$H NMR (CDCl$_3$) δ 0.66 (m, 2H), 0.84 (m, 2H), 1.05 (t, 6H), 1.57 (m, 2H), 1.70 (m, 2H), 2.96 (m, 1H), 7.33 (d, 1H), 7.44–7.49 (m, 3H), 7.54 (d, 1H), 8.69 (m, 1H), 8.77 (dd, 1H), 8.97 (s, 1H), 9.75 (br, NH). (NH$_2$ not observed).

Example 19

N-Isopropyl-1-[3-(3-quinolinylethynyl)phenyl]-1,4-dihydro[1,8]naphthyridin-4-one-3-carboxamide Following the procedure of EXAMPLE 15, but substituting N-isopropyl-1-(3-ethynylphenyl)-1,4-dihydro[1,8] naphthyridin-4-one-3-carboxamide from Step 2 of EXAMPLE 5 for 2-phenyl-3-butyn-2-ol, and 3-bromoquinoline for N-isopropyl-1-(3-bromophenyl)-1,4-dihydro[1,8]naphthyridin-4-one-3-carboxamide, the title compound was obtained as a solid.

$^1$H NMR (CDCl$_3$) δ 1.32 (d, 6H), 4.32 (m, 1H), 7.48–7.51 (m, 2H), 7.58–7.65 (m, 2H), 7.71 (s, 1H), 7.73–7.80 (m, 2H), 7.83 (d, 1H), 8.12 (d, 1H), 8.35 (s, 1H), 8.75 (m, 1H), 8.85 (dd, 1H), 9.02 (s, 1H), 9.06 (s, 1H), 9.65 (br, NH).

Example 20

N-Isopropyl-1-[3-(1-oxido-3-quinolinylethynyl) phenyl]-1,4-dihydro[1,8]naphthyridin-4-one-3-carboxamide Following the procedure of EXAMPLE 19, but substituting 3-bromoquinoline N-oxide for 3-bromoquinoline, the title compound was obtained as a solid.

¹H NMR (CDCl₃) δ 1.33 (d, 6H), 4.32 (m, 1H), 7.49–7.53 (m, 2H), 7.63 (t, 1H), 7.68–7.73 (m, 2H), 7.75–7.83 (m, 2H), 7.88–7.92 (m, 2H), 8.63 (s, 1H), 8.73–8.78 (m, 2H), 8.86 (dd, 1H), 9.05 (s, 1H), 9.67 (br, NH).

Example 21

N-Isopropyl-1-[3-(cyclopropylethynyl)phenyl]-1,4-dihydro[1,8]naphthyridin-4-one-3-carboxamide Following the procedure of EXAMPLE 15, but substituting cyclopropylacetylene (*Tetrahedron letters* 2000, 41, 4007) for 2-phenyl-3-butyn-2-ol, the title compound was obtained as a gray solid.

¹H NMR (CDCl₃) δ 0.83 (m, 2H), 0.90 (m, 2H), 1.31 (d, 6H), 1.48 (m, 1H), 4.31 (m, 1H), 7.33 (m, 1H), 7.45–7.51 (m, 3H), 7.55 (d, 1H), 8.72 (m, 1H), 8.83 (dd, 1H), 9.01 (s, 1H), 9.68 (br, NH).

Example 22

N-Isopropyl-1-[3-(6-amino-3-pyridinylethynyl)phenyl]-1,4-dihydro[1,8]naphthyridin-4-one-3-carboxamide Following the procedure of EXAMPLE 19, but substituting but substituting 5-bromo-2-aminopyridine for 3-bromoquinoline, the title compound was obtained as a solid.

¹H NMR (CDCl₃) δ 1.33 (d, 6H), 4.31 (m, 1H), 4.71 (br, NH₂), 6.49 (d, 1H), 7.40 (m, 1H), 7.48 (m, 1H), 7.54–7.60 (m, 3H), 7.68 (d, 1H), 8.28 (s, 1H), 8.72 (m, 1H), 8.83 (dd, 1H), 9.04 (s, 1H), 9.67 (br, NH).

Example 23

N-Isopropyl-1-{3-[5-(1-hydroxy-1-methylethyl)-1-oxido-3-pyridinylethynyl]phenyl}-1,4-dihydro[1,8]naphthyridin-4-one-3-carboxamide Step 1: 3-Bromo-5-(1-hydroxy-1-methylethyl)pyridine.

To a solution of ethyl 5-bromonicotinate (1.02 g, 4.4 mmol) in diethyl ether (15 mL) at −30° C. was added a 3M solution of methyl magnesium bromide in ether (4 mL, 12 mmol). The resulting slurry was refluxed for 2 hours then cooled and quenched with an excess of 0.5M aqueous monobasic sodium phosphate and partitioned between ether and water. The product from the organic phase was chromatographed on silica gel eluting with a 2:1:2 mixture of ether, pentane and ammonia-saturated methylene chloride to afford the 3-bromo-5-(1-hydroxy-1-methylethyl)pyridine compound as a yellow oil.

Step 2: 3-Bromo-5-(1-hydroxy-1-methylethyl)pyridine-N-oxide.

To a solution of 3-bromo-5-(1-hydroxy-1-methylethyl) pyridine from Step 1 (3.1 mmol) in chloroform (10 mL) was added m-chloroperoxybenzoic acid 70% (1.5 eq) and the resulting mixture was stirred at room temperature for 18 hours. An excess of calcium hydroxide was added and after stirring for 5 minutes, the mixture was filtered through celite and the filtrate was evaporated. The crude material was chromatographed on silica gel eluting with 10% ethanol in methylene chloride (saturated with ammonia) to afford the 3-bromo-5-(1-hydroxy-1-methylethyl)pyridine-N-oxide compound as a solid.

Step 3: N-Isopropyl-1-[3-[5-(1-hydroxy-1-methylethyl)-1-oxido-3-pyridinylethynyl]phenyl}-1,4-dihydro[1,8]naphthyridin-4-one-3-carboxamide.

Following the procedure of EXAMPLE 15, but substituting N-isopropyl-1-(3-ethynylphenyl)-1,4-dihydro[1,8]naphthyridin-4-one-3-carboxamide from EXAMPLE 5 for 2-phenyl-3-butyn-2-ol, and 3-bromo-5-(1-hydroxy-1-methylethyl)pyridine-N-oxide from Step 2 for N-isopropyl-1-(3-bromophenyl)-1,4-dihydro[1,8]naphthyridin-4-one-3-carboxamide, the N-isopropyl-1-{3-[5-(1-hydroxy-1-methylethyl)-1-oxido-3-pyridinylethynyl]phenyl}-1,4-dihydro[1,8]naphthyridin-4-one-3-carboxamide compound was obtained as a solid.

¹H NMR (CDCl₃) δ 1.32 (d, 6H), 1.64 (s, 6H), 2.22 (br, 1H, OH), 4.30 (m, 1H), 7.45–7.52 (m, 2H), 7.60 (t, 1H), 7.66 (s, 1H), 7.72 (d, 1H), 7.98 (s, 1H), 8.70 (br, 2H), 8.73 (m, 1H), 8.84 (dd, 1H), 9.03 (s, 1H), 9.68 (br, NH).

Example 24

N-Isopropyl-1-{3-[6-(1-hydroxy-1-methylethyl)-3-pyridinylethynyl]phenyl}-1,4-dihydro[1,8]naphthyridin-4-one-3-carboxamide Step 1: 5-Bromo-2-(1-hydroxy-1-methylethyl)pyridine.

To a suspension of 2,5-dibromopyridine in toluene (12 mL/mmol) cooled to −78° C. was added n-butyllithium 2.5M in hexanes (1.05 eq) and the resulting mixture was stirred in the cold for 2.5 hours. Acetone (2 eq) was added and stirring was continued for 1.5 h. After quenching with saturated aqueous ammonium chloride solution, the mixture was warmed to room temperature and partitioned between ethyl acetate and water. The product from the organic phase was chromatographed on silica gel eluting with 20% ethyl acetate in hexane to afford the 5-bromo-2-(1-hydroxy-1-methylethyl) pyridine compound as a syrup.

Step 2: 5-Bromo-2-(1-methyl-1-{[2-(trimethylsilyl)ethoxy]methoxy}ethyl)pyridine.

To a solution of 5-bromo-2-(1-hydroxy-1-methylethyl) pyridine from Step 1 (14 mmol) in methylene chloride (50 mL) at 0° C. was added N,N-diisopropylethylamine (37.3 mmol) and 2-(trimethylsilyl)ethoxymethyl chloride (15.3 mmol). The resulting mixture was stirred at room temperature for 18 hours, then refluxed for 24 hours. After cooling to room temperature the mixture was quenched with saturated aqueous ammonium chloride solution and partitioned between methylene chloride and water. The crude product from the organic phase was chromatographed on silica gel eluting with 6% ethyl acetate in hexane to afford the 5-bromo-2-(1-methyl-1-{[2-(trimethylsilyl)ethoxy]methoxy}ethyl)pyridine compound.

Step 3: 2-(1-Methyl-1-{[2-(trimethylsilyl)ethoxy]methoxy}ethyl)-5-[(trimethylsilyl)ethynyl]pyridine.

Following the procedure of Step 5 of EXAMPLE 1, but substituting the product from present Step 2 for N-isopropyl-1-(3-bromophenyl)-1,4-dihydro[1,8]naphthyridin-4-one-3-carboxamide and trimethylsilylacetylene for phenylacetylene, the 2-(1-methyl-1-{[2-(trimethylsilyl)ethoxy]methoxy}ethyl)-5-[(trimethylsilyl)ethynyl]pyridine compound was obtained.

Step 4: 5-Ethynyl-2-(1-methyl-1-{[2-(trimethylsilyl)ethoxy]methoxy}ethyl)pyridine.

Following the procedure of Step 2 of EXAMPLE 5, but substituting the product from present Step 3 for N-isopropyl-1-[3-(trimethylsilylethynyl)phenyl]-1,4-dihydro[1,8]naphthyridin-4-one-3-carboxamide, the 5-ethynyl-2-(1-methyl-1-{(trimethylsilyl)ethoxy]methoxy}ethyl)pyridine compound was obtained.

Step 5: N-Isopropyl-1-(3-{[6-(1-methyl-1-{{2-trimethylsilyl)ethoxy]methoxy}ethyl)pyridin-3-yl]ethynyl}phenyl)-1,4-dihydro[1,8]naphthyridin-4-one-3-carboxamide.

Following the procedure of Step 5 of EXAMPLE 1, but substituting the product from present Step 4 for phenylacetylene, the N-isopropyl-1-(3-{[6-(1-methyl-1-{{2-trimethylsilyl)ethoxy]methoxy}ethyl)pyridin-3-yl]ethynyl}phenyl)-1,4-dihydro[1,8]naphthyridin-4-one-3-carboxamide compound was obtained.

Step 6: N-Isopropyl-1-3-[6-(1-hydroxy-1-methylethyl)-3-pyridinylethynyl]phenyl}-1,4-dihydro[1,8]naphthyridin-4-one-3-carboxamide.

To a solution of N-isopropyl-1-(3-{[6-(1-methyl-1-{{2-trimethylsilyl)ethoxy]methoxy}ethyl)pyridin-3-yl]ethynyl}phenyl)-1,4-dihydro[1,8]naphthyridin-4-one-3-carboxamide product from present Step 5 in methylene chloride (32 mL/mmol) at 0° C. was added trifluoroacetic acid (3.2 mL/mmol). The resulting mixture was stirred at 0° C. for 2 hours then at room temperature for 2 hours. The mixture was neutralized slowly with saturated aqueous sodium bicarbonate and partitioned between methylene chloride and water. The crude material from the organic phase was chromatographed on silica gel eluting with 40% ether in methylene chloride and the purified product was stirred in ether at room temperature for 2 hours and filtered to afford the N-isopropyl-1-{3-[6-(1-hydroxy-1-methylethyl)-3-pyridinylethynyl]phenyl}-1,4-dihydro[1,8]naphthyridin-4-one-3-carboxamide compound as solid.

$^1$H NMR (Acetone-d$_6$) δ 1.24 (d, 6H), 1.50 (s, 6H), 4.18 (m, 1H), 4.57 (s, 1H, OH), 7.61 (m, 1H), 7.69–7.74 (m, 3H), 7.78 (m, 1H), 7.88 (s, 1H), 7.93 (dd, 1H), 8.68 (s, 1H), 8.74 (m, 1H), 8.78 (dd, 1H), 8.88 (s, 1H), 9.63 (br, NH).

Example 25

N-Isopropyl-1-{3-[6-(1-hydroxy-1-methylethyl)-1-oxido-3-pyridinylethynyl]phenyl}-1,4-dihydro[1,8]naphthyridin-4-one-3-carboxamide Following the procedure of Step 2 of EXAMPLE 23, but substituting N-isopropyl-1-{3-[6-(1-hydroxy-1-methylethyl)-3-pyridinylethynyl]phenyl}-1,4-dihydro[1,8]naphthyridin-4-one-3-carboxamide from example 24 for 3-bromo-5-(1-hydroxy-1-methylethyl)pyridine, the title compound was obtained as a solid.

$^1$H NMR (Acetone-d$_6$) δ 1.25 (d, 6H), 1.60 (s, 6H), 4.18 (m, 1H), 7.24 (s, 1H, OH), 7.60–7.63 (m, 3H), 7.72–7.78 (m, 2H), 7.82 (d, 1H), 7.91 (s, 1H) 1H), 8.74 (m, 1H), 8.78 (dd, 1H), 8.87 (s, 1H), 9.62 (br, NH).

Example 26

N-Isopropyl-1-{3-[4-(1-hydroxy-1-methylethyl)-2-pyridinylethynyl]phenyl}-1,4-dihydro[1,8]naphthyridin-4-one-3-carboxamide Step 1: Methyl 2-bromoisonicotinate.

To a solution of 2-bromoisonicotinic acid (Chem. Pharm. Bull. 1990, 38, 2446) (2.0 g) in tetrahydrofuran (100 mL) was added excess ethereal diazomethane and the resulting mixture was stirred at room temperature for 1 hour. The mixture was evaporated and the product chromatographed on silica gel eluting with a 1:3 mixture of ethyl acetate and hexane to afford the methyl 2-bromoisonicotinate ester as a colorless liquid.

Step 2: 2-Bromo-4-(1-hydroxy-1-methylethyl)i)pyridine.

Following the procedure of Step 1 of EXAMPLE 23, but substituting methyl 2-bromoisonicotinate from present Step 1 for ethyl 5-bromonicotinate, the 2-bromo-4-(1-hydroxy-1-methylethyl)pyridine compound was obtained as a white solid.

Step 3: N-Isopropyl-1-{3-[4-(1-hydroxy-1-methylethyl)-2-pyridinylethynyl]phenyl}-1,4-dihydro[1,8]naphthyridin-4-one-3-carboxamide.

Following the procedure of EXAMPLE 19, but substituting the 2-bromo-4-(1-hydroxy-1-methylethyl)pyridine from present Step 2 for 3-bromoquinoline, the N-isopropyl-1-{3-[4-(1-hydroxy-1-methylethyl)-2-pyridinylethynyl]phenyl}-1,4-dihydro[1,8]naphthyridin-4-one-3-carboxamide compound was obtained as a yellow foam.

$^1$H NMR (Acetone-d$_6$) δ 1.27 (d, 6H), 1.55 (s, 6H), 4.20 (m, 1H), 4.42 (s, 1H, OH), 7.52 (m, 1H), 7.63 (m, 1H), 7.72–7.79 (m, 3H), 7.84 (d, 1H), 7.95 (s, 1H), 8.55 (d, 1H), 8.77 (m, 1H), 8.80 (dd, 1H), 8.92 (s, 1H), 9.65 (br, NH).

Example 27

N-Isopropyl-1-{3-[5-(1-hydroxy-1-methylethyl)-2-pyridinylethynyl]phenyl }-1,4-dihydro[1,8]naphthyridin-4-one-3-carboxamide Step 1: 2-Bromo-5-(1-hydroxy-1-methylethyl)pyridine.

A solution of 2,5-dibromopyridine in diethyl ether (5 mL/mmol) was cooled to −78° C., and n-butyllithium 2.5M in hexanes (1.05 eq) was added slowly. After 2 hrs in the cold, acetone (1.3 eq) was added and stirring was continued for 1 hour. The resulting mixture was quenched with saturated aqueous ammonium chloride solution, warmed to room temperature, and partitioned between ether and water. The crude product from the organic phase was triturated with 1:1 ether-hexane and filtered to afford the 2-bromo-5-(1-hydroxy-1-methylethyl)pyridine compound as a solid.

Step 2: 5-(1-Hydroxy-1-methylethyl)-2-[(trimethylsilyl)ethynyl]pyridine.

Following the procedure of EXAMPLE 15, but substituting the product 2-bromo-5-(1-hydroxy-1-methylethyl)pyridine from present Step 1 for N-isopropyl-1-(3-bromophenyl)-1,4-dihydro[1,8]naphthyridin-4-one-3-carboxamide and trimethylsilylacetylene for 2-phenyl-3-butyn-2-ol, the 5-(1-hydroxy-1-methylethyl)-2-[(trimethylsilyl)ethynyl]pyridine compound was obtained.

Step 3: 2-Ethynyl-5-(1-hydroxy-1-methylethyl)pyridine.

Following the procedure of Step 2 of EXAMPLE 5, but substituting the product 5-(1-hydroxy-1-methylethyl)-2-[(trimethylsilyl)ethynyl]pyridine from present Step 2 for N-isopropyl-1-[3-(trimethylsilylethynyl)phenyl]-1,4-dihydro[1,8]naphthyridin-4-one-3-carboxamide, the 2-ethynyl-5-(1-hydroxy-1-methylethyl)pyridine compound was obtained.

Step 4: N-Isopropyl-1-{3-[5-(1-hydroxy-1-methylethyl)-2-pyridinylethynyl]phenyl}-1,4-dihydro[1,8]naphthyridin-4-one-3-carboxamide.

Following the procedure of EXAMPLE 15 but substituting the product 2-ethynyl-5-(1-hydroxy-1-methylethyl)pyridine from present Step 3 for 2-phenyl-3-butyn-2-ol, the N-Isopropyl-1-{3-[5-(1-hydroxy-1-methylethyl)-2-pyridinylethynyl]phenyl}-1,4-dihydro[1,8]naphthyridin-4-one-3-carboxamide compound was obtained.

$^1$H NMR (CDCl$_3$) δ 1.32 (d, 6H), 1.66 (s, 6H), 2.08 (s, 1H, OH), 4.31 (m, 1H), 7.46–7.55 (m, 3H), 7.61 (t, 1H), 7.71 (s, 1H), 7.78 (d, 1H), 7.86 (dd, 1H), 8.73 (m, 1H), 8.77 (m, 1H), 8.83 (dd, 1H), 9.04 (s, 1H), 9.67 (br, NH).

Example 28

N-Isopropyl-1-{3-[6-(1-hydroxy-1-methylethyl)-2-pyridinylethynyl]phenyl}-1,4-dihydro [1,8] naphthyridin-4-one-3-carboxamide Step 1: 2-Bromo-6-(1-hydroxy-1-methylethyl)pyridine.

Following the procedure of Step 1 of EXAMPLE 27, but substituting 2,6-dibromopyridine for 2,5-dibromopyridine, the 2-Bromo-6-(1-hydroxy-1-methylethyl)pyridine compound was obtained as a solid.

Step 2: N-Isopropyl-1-{3-[6-(1-hydroxy-1-methylethyl)-2-pyridinylethynyl]phenyl}-1,4-dihydro[1,8]naphthyridin-4-one-3-carboxamide.

Following the procedure of EXAMPLE 19, but substituting the product 2-Bromo-6-(1-hydroxy-1-methylethyl) pyridine from present Step 1 for 3-bromoquinoline, the N-Isopropyl-1-{3-[6-(1-hydroxy-1-methylethyl)-2-pyridinylethynyl]phenyl}-1,4-dihydro[1,8]naphthyridin-4-one-3-carboxamide compound was obtained.

$^1$H NMR (CDCl$_3$) δ 1.31 (d, 6H), 1.58 (s, 6H), 4.32 (m, 1H), 4.83 (s, 1H, OH), 7.38 (d, 1H), 7.43–7.52 (m, 3H), 7.60 (t, 1H), 7.70–7.75 (m, 2H), 7.79 (d, 1H), 8.74 (m, 1H), 8.84 (dd, 1H), 9.03 (s, 1H), 9.66 (br, NH).

Example 29

N-Cyclopropyl-1-{3-[6-(1-hydroxy-1-methylethyl)-1-oxido-3-pyridinylethynyl]phenyl}-1,4-dihydro[1,8]naphthyridin-4-one-3-carboxamide Step 1: 5-Bromo-2-(1-hydroxy-1-methylethyl)pyridine N-oxide.

Following the procedure of Step 2 of EXAMPLE 23, but substituting 5-bromo-2-(1-hydroxy-1-methylethyl)pyridine from Step 1 of EXAMPLE 24 for 3-bromo-5-(1-hydroxy-1-methylethyl)pyridine, the 5-Bromo-2-(1-hydroxy-1-methylethyl)pyridine N-oxide compound was obtained.

Step 2: N-Cyclopropyl-1-{3-[6-(1-hydroxy-1-methylethyl)-1-oxido-3-pyridinylethynyl]phenyl}-1,4-dihydro[1,8]naphthyridin-4-one-3-carboxamide.

Following the procedure of EXAMPLE 15, but substituting N-cyclopropyl-1-(3-ethynylphenyl)-1,4-dihydro[1,8]naphthyridin-4-one-3-carboxamide from EXAMPLE 6 for 2-phenyl-3-butyn-2-ol and 5-bromo-2-(1-hydroxy-1-methylethyl)pyridine-N-oxide from present Step 1 for N-isopropyl-1-(3-bromophenyl)-1,4-dihydro[1,8]naphthyridin-4-one-3-carboxamide, the N-cyclopropyl-1-{3-[6-(1-hydroxy-1-methylethyl)-1-oxido-3-pyridinylethynyl]phenyl}-1,4-dihydro[1,8]naphthyridin-4-one-3-carboxamide compound was obtained as a solid.

$^1$H NMR (CDCl$_3$) δ 0.66 (m, 2H), 0.84 (m, 2H), 1.66 (s, 6H), 2.96 (m, 1H), 7.34 (d, 1H), 7.43–7.50 (m, 4H), 7.58–7.62 (m, 2H), 7.69 (d, 1H), 8.33 (s, 1H), OH), 8.69 (m, 1H), 8.79 (dd, 1H), 8.99 (s, 1H), 9.73 (br, NH).

Example 30

N-Isopropyl-1-{3-[(4-pyridin-3-ylphenyl)ethynyl]phenyl}-1,4-dihydro[1,8]naphthyridin-4-one-3-carboxamide Step 1: 3-(4-Bromophenyl)pyridine.

A mixture of pyridine-3-boronic acid 1,3-propanediol cyclic ester, 4-bromoiodobenzene (1.1 eq), [1,1 '-bis(diphenylphosphino)ferrocene]dichloropalladium(II) (0.05 eq) and 2M aqueous sodium carbonate (5 eq) in N,N-dimethylformamide (2 ml/mmol) was stirred at 85° C. for 4 hours. After quenching with saturated aqueous ammonium chloride solution the mixture was partitioned between ethyl acetate and water and the crude product from the organic phase was chromatographed on silica gel eluting with a 1:9 mixture of ethyl acetate and hexane to afford the 3-(4-bromophenyl)pyridine compound as a solid.

Step 2: N-Isopropyl-1-}3-[(4-pyridin-3-ylphenyl)ethynyl]phenyl}-1,4-dihydro[1,8]naphthyridin-4-one-3-carboxamide.

Following the procedure of EXAMPLE 19, but substituting the product from present Step 1 for 3-bromoquinoline, the N-isopropyl-1-{3-[(4-pyridin-3-ylphenyl)ethynyl]phenyl}-1,4-dihydro[1,8]naphthyridin-4-one-3-carboxamide compound was obtained.

$^1$H NMR (CDCl$_3$) δ 1.28 (d, 6H), 4.28 (m, 1H), 7.38 (m, 1H), 7.42 (d, 1H), 7.48 (m, 1H), 7.53–7.64 (m, 6H), 7.70 (d, 1H), 7.88 (d, 1H), 8.60 (m, 1H), 8.71 (m, 1H), 8.82 (dd, 1H), 8.86 (s, 1H), 9.02 (s, 1H), 9.63 (br, NH).

Example 31

N-Isopropyl-1-(3-{[5-(1-hydroxy-1-methylethyl)thien-2-yl]ethynyl}phenyl)-1,4-dihydro[1,8]naphthyridin-4-one-3-carboxamide Step 1: 2-Bromo-5-(1-hydroxy-1-methylethyl)thiophene.

To a solution of 2-acetyl-5-bromothiophene in THF (2.5 mL/mmol) at −30° C. was added 1.4M methylmagnesium bromide in 3:1 toluene-THF (1.5 eq) and the resulting mixture was warmed to −10° C. and stirred for 1.5 hours. After quenching with saturated aqueous ammonium chloride solution, the mixture was partitioned between ether and water. The organic fraction was dried and evaporated, and the crude material was chromatographed on silica gel eluting with a 1:4 mixture of ether and hexane to afford the 2-bromo-5-(1-hydroxy-1-methylethyl)thiophene compound.

Step 2: 2-(1-Hydroxy-1-methylethyl)-5-trimethylsilylethynyl]thiophene.

Following the procedure of EXAMPLE 15, but substituting the product from present Step 1 for N-isopropyl-1-(3-bromophenyl)-1,4-dihydro[1,8]naphthyridin-4-one-3-carboxamide and trimethylsilylacetylene for 2-phenyl-3-butyn-2-ol, the 2-(1-hydroxy-1-methylethyl)-5-trimethylsilylethynyl thiophene compound was obtained.

Step 3: 2-Ethynyl-5-(1-hydroxy-1-methylethyl)thiophene.

Following the procedure of Step 2 of EXAMPLE 5, but substituting the product from present Step 2 for N-isopropyl-1-[3-(trimethylsilylethynyl)phenyl]-1,4-dihydro[1,8]naphthyridin-4-one-3-carboxamide, the 2-ethynyl-5-(1-hydroxy-1-methylethyl)thiophene compound was obtained.

Step 4: N-Isopropyl-1-(3-{[5-(1-hydroxy-1-methylethyl)thien-2-yl]ethynyl}phenyl)-1,4-dihydro[1,8]naphthyridin-4-one-3-carboxamide.

Following the procedure of EXAMPLE 15, but substituting the 2-ethynyl-5-(1-hydroxy-1-methylethyl)thiophene product from present Step 3 for 2-phenyl-3-butyn-2-ol, the N-isopropyl-1-(3-{[5-(1-hydroxy-1-methylethyl)thien-2-yl]ethynyl}phenyl)-1,4-dihydro[1,8]naphthyridin-4-one-3-carboxamide compound was obtained as a solid.

$^1$H NMR (CDCl$_3$) δ 1.31 (d, 6H), 1.70 (s, 6H), 2.42 (s, 1H, OH), 4.31 (m, 1H), 6.87 (d, 1H), 7.16 (d, 1H), 7.42 (d, 1H), 7.48 (m, 1H), 7.59 (t, 1H), 7.63 (s, 1H), 7.68 (d, 1H), 8.73 (m, 1H), 8.84 (dd, 1H), 9.02 (s, 1H), 9.68 (br, NH).

Example 32

N-Isopropyl-1-(3-{[2-(1-hydroxy-1-methylethyl)-1,3-thiazol-5-yl]ethynyl}phenyl)-1,4-dihydro[1,8] naphthyridin-4-one-3-carboxamide Step 1: 2-(1-hydroxy-1-methylethyl) thiazole.

To a solution of thiazole in ether (1 mL/mmol) at −78° C. was added 2.2M n-butyllithium in hexanes (1.1 eq) and the resulting mixture was stirred for 30 minutes. Acetone (1.2 eq) was added and the mixture was stirred at −78° C. for a further 30 minutes. The mixture was quenched in the cold with saturated aqueous ammonium chloride solution and warmed to room temperature, then partitioned between ether and water. The organic phase was dried and evaporated to yield the crude product as an orange-brown oil which was used as such in the next step.

Step 2: 2-(1-methyl-1-{[2-(trimethylsilyl)ethoxy]methoxy}ethyl)thiazole.

Following the procedure of Step 2 of EXAMPLE 24, but substituting the product from present Step 1 for 5-bromo-2-(1-hydroxy-1-methylethyl) pyridine, the 2-(1-methyl-1-{[2-(trimethylsilyl)ethoxy]methoxy}ethyl)thiazole compound was obtained as an oil.

Step 3: 5-Bromo-2-(1-hydroxy-1-methylethyl)thiazole.

To a solution of 2-(1-methyl-1-{[2-(trimethylsilyl)ethoxy]methoxy}ethyl)thiazole from Step 2 in chloroform (2 mL mmol) at room temperature was added bromine (2 molar eq) and the resulting mixture was stirred for 1 hour. Solid sodium bicarbonate (0.55 eq) was added and the mixture was stirred for 5 hours. More sodium bicarbonate was added (0.55 eq) and stirring was continued for 18 hours. After a final addition of sodium bicarbonate (0.55 eq) the mixture was stirred for a further 5 hours, diluted with chloroform and the organic phase was washed with saturated aqueous sodium bicarbonate, then with water, dried and evaporated. The crude material was chromatographed, eluting with a 3:7 mixture of ethyl acetate and hexane to afford the desired product.

Step 4: N-Isopropyl-1-(3-{[2-(1-hydroxy-1-methylethyl)-1,3-thiazol-5-yl]ethynyl}phenyl)-1,4-dihydro[1,8]naphthyridin-4-one-3-carboxamide.

Following the procedure of EXAMPLE 19, but substituting the product from present Step 3 for 3-bromoquinoline, the N-isopropyl-1-(3-{[2-(1-hydroxy-1-methylethyl)-1,3-thiazol-5-yl]ethynyl}phenyl)-1,4-dihydro[1,8]naphthyridin-4-one-3-carboxamide compound was obtained as a solid.

$^1$H NMR (CDCl$_3$) δ 1.29 (d, 6H), 1.68 (s, 6H), 2.90 (s, 1H, OH), 4.28 (m, 1H), 7.42 (d, 1H), 7.46 (m, 1H), 7.54–7.60 (m, 2H), 7.66 (d, 1H), 7.82 (s, 1H), 8.70 (m, 1H), 8.80 (dd, 1H), 8.99 (s, 1H), 9.63 (br, NH).

EXAMPLE 33

1-[3-(1-Oxido-3-pyridinylethynyl)phenyl]-1,4-dihydro[1,8]naphthyridin-4-one-3-carboxamide Step 1: 1-(3-Bromophenyl)-1,4-dihydro[1,8]naphthyridin-4-one-3-carboxamide.

Following the procedure of Step 4 of EXAMPLE 1, but substituting 28% aqueous ammonium hydroxide for isopropylamine, the 1-(3-bromophenyl)-1,4-dihydro[1,8]naphthyridin-4-one-3-carboxamide compound was obtained as a solid.

Step 2: 1-[3-(Trimethylsilylethynyl)phenyl[-1,4-dihydro[1,8]naphthyridin-4-one-3-carboxamide.

Following the procedure of Step 5 of EXAMPLE 1, but substituting the 1-(3-Bromophenyl)-1,4-dihydro[1,8]naphthyridin-4-one-3-carboxamide from Step 1 for N-isopropyl-1-(3-bromophenyl)-1,4-dihydro[1,8]naphthyridin-4-one-3-carboxamide and trimethylsilylacetylene for phenylacetylene, the 1-[3-(trimethylsilylethynyl)phenyl]-1,4-dihydro[1,8]naphthyridin-4-one-3-carboxamide product was obtained as a solid.

Step 3: 1-(3-Ethynylphenyl)-1,4-dihydro[1,8]naphthyridin-4-one-3-carboxamide.

To a solution of 1-[3-(trimethylsilylethynyl)phenyl]-1,4-dihydro[1,8]naphthyridin-4-one-3-carboxamide from Step 2 in THF (30 mL/mmol) at 0° C. was added 1M tetrabutylammonium fluoride in THF (1.5 eq) and the resulting mixture was stirred at 0° C. for 30 minutes. The mixture was partitioned between methylene chloride and water and the organic phase was dried and evaporated. The crude 1-(3-ethynylphenyl)-1,4-dihydro[1,8]naphthyridin4-one-3-carboxamide product was used as such in the next step.

Step 4: 1-[3-(1-Oxido-3-pyridinylethynyl)phenyl]-1,4-dihydro[1,8]naphthyridin-4-one-3-carboxamide.

Following the procedure of example 19, but substituting the 1-(3-ethynylphenyl)-1,4-dihydro[1,8]naphthyridin4-one-3-carboxamide from Step 3 for N-Isopropyl-1-(3-ethynylphenyl)-1,4-dihydro[1,8]naphthyridin-4-one-3-carboxamide and 3-bromopyridine N-oxide for 3-bromoquinoline, the 1-[3-(1-oxido-3-pyridinylethynyl)phenyl]-1,4-dihydro[1,8]naphthyridin4-one-3-carboxamide was obtained as a white solid.

$^1$H NMR (CDCl$_3$) δ 5.84 (br, 1H, NH), 7.30 (m, 1H), 7.41 (d, 1H), 7.53 (m, 2H), 7.64 (t, 1H), 7.67 (s, 1H), 7.74 (d, 1H), 8.21 (d, 1H), 8.35 (s, 1H), 8.75 (m, 1H), 8.88 (dd, 1H), 9.05 (s, 1H), 9.52 (br, 1H, NH).

Example 34

1-[3-(1-Oxido-3-pyridinylethynyl)phenyl]-1,4-dihydro[1,8]naphthyridin-4-one-3-carboxylic Acid Step 1: Ethyl 1-(3-Ethynylphenyl)-1,4-dihydro[1,8]naphthyridin-4-one-3-carboxylate.

Following the procedures of Steps 1 and 2 of EXAMPLE 5, but substituting ethyl 1-(3-bromophenyl)-1,4-dihydro[1,8]naphthyridin-4-one-3-carboxylate from Step 2 of EXAMPLE 1 for N-isopropyl-1-(3-bromophenyl)-1,4-dihydro[1,8]naphthyridin-4-one-3-carboxamide as the starting material, the Ethyl 1-(3-Ethynylphenyl)-1,4-dihydro[1,8]naphthyridin-4-one-3-carboxylate compound was obtained as a solid.

Step 2: Ethyl 1-[3-(1-Oxido-3-pyridinylethynyl)phenyl]-1,4-dihydro[1,8]naphthyridin-4-one-3-carboxylate.

Following the procedure of EXAMPLE 15, but substituting the ethyl 1-(3-ethynylphenyl)-1,4-dihydro[1,8]naphthyridin-4-one-3-carboxylate from present Step 1 for 2-phenyl-3-butyn-2-ol and 3-bromopyridine N-oxide for N-isopropyl-1-(3-bromophenyl)-1,4-dihydro[1,8]naphthyridin4-one-3-carboxamide, the ethyl 1-[3-(1-oxido-3-pyridinylethynyl)phenyl]-1,4-dihydro[1,8]naphthyridin-4-one-3-carboxylate was obtained as a solid.

Step 3: 1-[3-(1-Oxido-3-pyridinylethynyl)phenyl]-1,4-dihydro[1,8]naphthyridin-4-one-3-carboxylic acid.

Following the procedure of Step 3 of EXAMPLE 1, but substituting the ethyl 1-[3-(1-oxido-3-pyridinylethynyl)phenyl]-1,4-dihydro[1,8]naphthyridin-4-one-3-carboxylate ester from present Step 2 for ethyl 1-(3-bromophenyl)-1,4-dihydro[1,8]naphthyridin-4-one-3-carboxylate, the 1-[3-(1-oxido-3-pyridinylethynyl)phenyl]-1,4-dihydro[1,8]naphthyridin-4-one-3-carboxylic acid was obtained as a white solid.

$^1$H NMR (DMSO-d$_6$) δ 7.46 (t, 1H), 7.51 (d, 1H), 7.70 (t, 1H), 7.75 (m, 2H), 7.80 (d, 1H), 7.92 (s, 1H), 8.26 (d, 1H), 8.47 (s, 1H), 8.81 (dd, 1H), 8.89 (m, 1H), 8.97 (s, 1H).

Other variations or modifications, which will be obvious to those skilled in the art, are within the scope and teachings of this invention. This invention is not to be limited except as set forth in the following claims.

What is claimed is:

1. A compound represented by Formula (I):

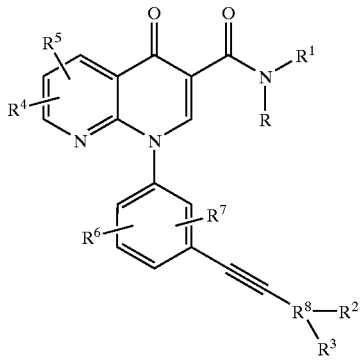

(I)

or a pharmaceutically acceptable salt thereof, wherein
R is H, —$C_{1-6}$alkyl or —$C_{3-6}$cycloalkyl;
$R^1$ is H, or a —$C_{1-6}$alkyl, —$C_{3-6}$cycloalkyl, —$C_{1-6}$alkoxy, —$C_{2-6}$alkenyl, —$C_{3-6}$alkynyl, —C(O)—$C_{1-6}$alkyl, —C(O)-aryl, —$C_{0-6}$alkyl)—$SO_n$—($C_{1-6}$alkyl), —$C_{0-6}$alkyly)—$SO_n$—(aryl), phenyl, wherein aryl is selected from phenyl or naphthyl and wherein any of the groups is optionally substituted with 1–3 independent —$C_{1-6}$alkyl, —$C_{1-6}$alkoxy, OH, —N($C_{0-6}$alkyl)($C_{0-6}$alkyl), —($C_{0-6}$alkyly)—$SO_n$—($C_{1-6}$alkyl), nitro, CN, =N—O—$C_{1-6}$alkyl, —O—N=$C_{1-6}$alkyl, or halogen substituents;
$R^2$ is absent, H, halogen, —$C_{1-6}$alkyl, —$C_{3-6}$cycloalkyl, —$C_{1-6}$alkyl($C_{3-6}$cycloalkyl)($C_{3-6}$cycloalkyl), —$C_{1-6}$alkoxy, phenyl, nitro, CN, =N—O—$C_{1-6}$alkyl, —O—N=$C_{1-6}$alkyl, —N($C_{0-6}$alkyl)($C_{0-6}$alkyl), —$NHSO_n$—($C_{1-6}$alkyl), —NHC(O)—$C_{1-6}$alkyl, —C(O)—$C_{1-6}$alkyl, —C(O)—O—$C_{1-6}$alkyl, —$C_{1-6}$alkyl(=N—OH), —C(N=NOH)$C_{1-6}$alkyl, —$C_{0-6}$alkyl(oxy)$C_{1-6}$alkyl-phenyl, —$SO_n$NH($C_{0-6}$alkyl), or —($C_{0-6}$alkyl)—$SO_n$—($C_{1-6}$alkyl), wherein the phenyl, is optionally substituted with halogen, —$C_{1-6}$alkyl, —$C_{1-6}$alkoxy, hydroxy, —N($C_{0-6}$alkyl)($C_{0-6}$alkyl), or —C(O)—O—$C_{1-6}$alkyl, and any alkyl is optionally substituted with 1–6 independent halogen or —OH substituents;
n is 0, 1, or 2;
$R^3$ is absent, H, OH, —N($C_{0-6}$alkyl)($C_{0-6}$alkyl), halogen or $C_{1-6}$alkyl, wherein any alkyl is optionally substituted with 1–6 independent halogen, OH, or —N($C_{0-6}$alkyl)($C_{0-6}$alkyl) substituents;
$R^4$, $R^5$, $R^6$, and $R^7$ each independently is H, halogen, —$C_{1-6}$alkyl, —$C_{1-6}$alkoxy, —$SO_n$—($C_{1-6}$alkyl), nitro, CN, or —N($C_{0-6}$alkyl)($C_{0-6}$alkyl), and any alkyl is optionally substituted with 1–6 independent halogen or —OH substituents; and
$R^8$ is pyridyl or pyridonyl, or pyridyl N-oxide.

2. The compound according to claim 1, or a pharmaceutically acceptable salt thereof, wherein
$R^8$ is pyridyl, or pyridyl N-oxide.

3. The compound according to claim 1, consisting of
N-Isopropyl-1-[3-(2-pyridinylethynyl)phenyl]-1,4-dihydro[1,8]naphthyridin-4-one-3-carboxamide;
N-Isopropyl-1-[3-(4-pyridinylethynyl)phenyl]-1,4-dihydro[1,8]naphthyridin-4-one-3-carboxamide;
N-Isopropyl-1-[3-(1-oxido-4-pyridinylethynyl)phenyl]-1,4-dihydro[1,8]naphthyridin-4-one-3-carboxamide;
N-Isopropyl-1-[3-(3-pyridinylethynyl)phenyl]-1,4-dihydro[1,8]naphthyridin-4-one-3-carboxamide;
N-Isopropyl-1-[3-(1-oxido-3-pyridinylethynyl)phenyl]-1,4-dihydro[1,8]naphthyridin-4-one-3-carboxamide;
N-Cyclopropyl-1-[3-(3-pyridinylethynyl)phenyl]-1,4-dihydro[1,8]naphthyridin-4-one-3-carboxamide;
N-Cyclopropyl-1-[3-(1-oxido-3-pyridinylethynyl)phenyl]-1,4-dihydro[1,8]naphthyridin-4-one-3-carboxamide;
N-Isopropyl-1-[3-(6-amino-3-pyridinylethynyl)phenyl]-1,4-dihydro[1,8]naphthyridin4-one-3-carboxamide;
N-Isopropyl-1-{3-[5-(1-hydroxy-1-methylethyl)-1-oxido-3-pyridinylethynyl]phenyl}-1,4-dihydro[1,8]naphthyridin-4-one-3-carboxamide;
N-Isopropyl-1- {3-[6-(1-hydroxy-1-methylethyl)-3-pyridinylethynyl]phenyl}-1,4-dihydro[1,8]naphthyridin-4-one-3-carboxamide;
N-Isopropyl-1-{3-[6-(1-hydroxy-1-methylethyl)-1-oxido-3-pyridinylethynyl]phenyl}-1,4-dihydro[1,8]naphthyridin-4-one-3-carboxamide;
N-Isopropyl-1-{3-[4-(1-hydroxy-1-methylethyl)-2-pyridinylethynyl]phenyl}-1,4-dihydro[1,8]naphthyridin-4-one-3-carboxamide;
N-Isopropyl-1-{3-[5-(1-hydroxy-1-methylethyl)-2-pyridinylethynyl]phenyl}-1,4-dihydro[1,8]naphthyridin-4-one-3-carboxamide;
N-Isopropyl-1-{3-[6-(1-hydroxy-1-methylethyl)-2-pyridinylethynyl]phenyl}-1,4-dihydro[1,8]naphthyridin-4-one-3-carboxamide;
N-Cyclopropyl-1-{3-[6-(1-hydroxy-1-methylethyl)-1-oxido-3-pyridinylethynyl]phenyl}-1,4-dihydro[1,8]naphthyridin-4-one-3-carboxamide;
1-[3-(1-Oxido-3-pyridinylethynyl)phenyl]-1,4-dihydro[1,8]naphthyridin-4-one-3-carboxamide; or
1-[3-(1-Oxido-3-pyridinylethynyl)phenyl]-1,4-dihydro[1,8]naphthyridin-4-one-3-carboxylic acid;
or a pharmaceutically acceptable salt thereof.

4. A pharmaceutical composition comprising
a therapeutically effective amount of the compound according to claim 1 or a pharmaceutically acceptable salt thereof; and
a pharmaceutically acceptable carrier.

5. The compound according to claim 1, which is
N-Cyclopropyl-1-[3-(3-pyridinylethynyl)phenyl]-1,4-dihydro[1,8]naphthyridin-4-one-3-carboxamide;
or a pharmaceutically acceptable salt thereof.

6. A pharmaceutical composition comprising
a therapeutically effective amount of the compound according to claim 5 or a pharmaceutically acceptable salt thereof; and
a pharmaceutically acceptable carrier.

7. The compound according to claim 1, which is
N-Cyclopropyl-1-[3-(1-oxido-3-pyridinylethynyl)phenyl]-1,4-dihydro[1,8]naphthyridin-4-one-3-carboxamide;
or a pharmaceutically acceptable salt thereof.

8. A pharmaceutical composition comprising
a therapeutically effective amount of the compound according to claim 7 or a pharmaceutically acceptable salt thereof; and
a pharmaceutically acceptable carrier.

9. A compound according to claim 1 wherein R is Hydrogen.

10. A compound according to claim 1 wherein $R^4$, $R^5$, $R^6$ and $R^7$ are each hydrogen.

11. A compound according to claim 1 wherein $R^1$ is $-C_{3-6}$cycloalkyl.

12. A compound according to claim 1 wherein R is Hydrogen; and $R^4$, $R^5$, $R^6$ and $R^7$ are each hydrogen.

13. A compound according to claim 12 wherein $R^8$ is pyridyl or pyridyl N-oxide.

14. A compound according to claim 12 wherein $R^1$ is $_3$_cycloalkyl.

15. A pharmaceutical composition comprising a therapeutically effective amount of the compound according to claim 2 or a pharmaceutically acceptable salt thereof; and a pharmaceutically acceptable carrier.

16. A pharmaceutical composition comprising a therapeutically effective amount of the compound according to claim 12 or a pharmaceutically acceptable salt thereof; and a pharmaceutically acceptable carrier.

* * * * *

UNITED STATES PATENT AND TRADEMARK OFFICE
CERTIFICATE OF CORRECTION

PATENT NO. : 6,743,802 B2  
DATED : June 1, 2004  
INVENTOR(S) : Daniel Guay et al.

It is certified that error appears in the above-identified patent and that said Letters Patent is hereby corrected as shown below:

<u>Column 53,</u>  
Line 13, delete "₃.cycloalkyl'" and insert -- -$C_{3-6}$ cycloalkyl" --.

Signed and Sealed this

Thirtieth Day of May, 2006

JON W. DUDAS  
*Director of the United States Patent and Trademark Office*